Figure 1:
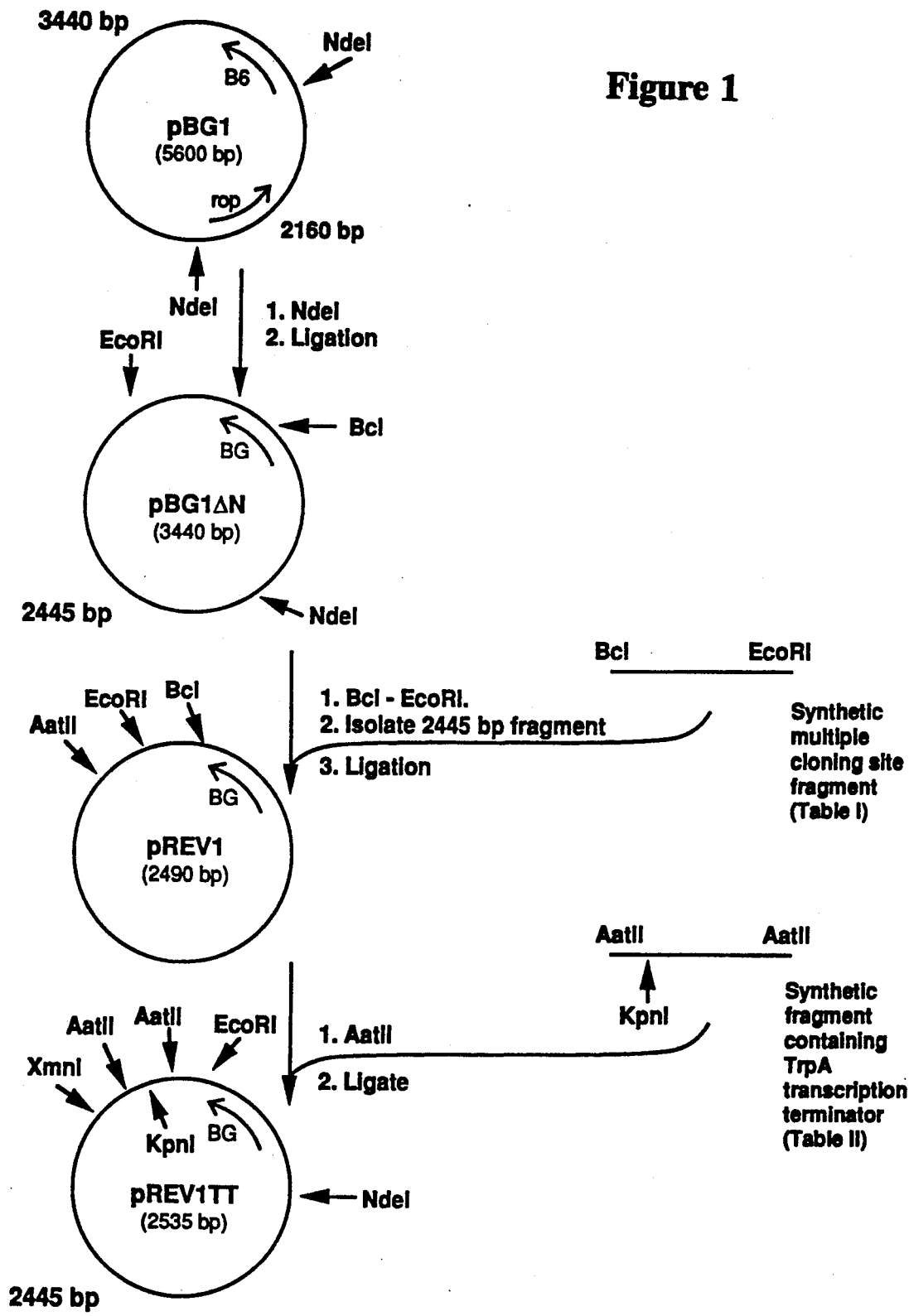
Figure 1:
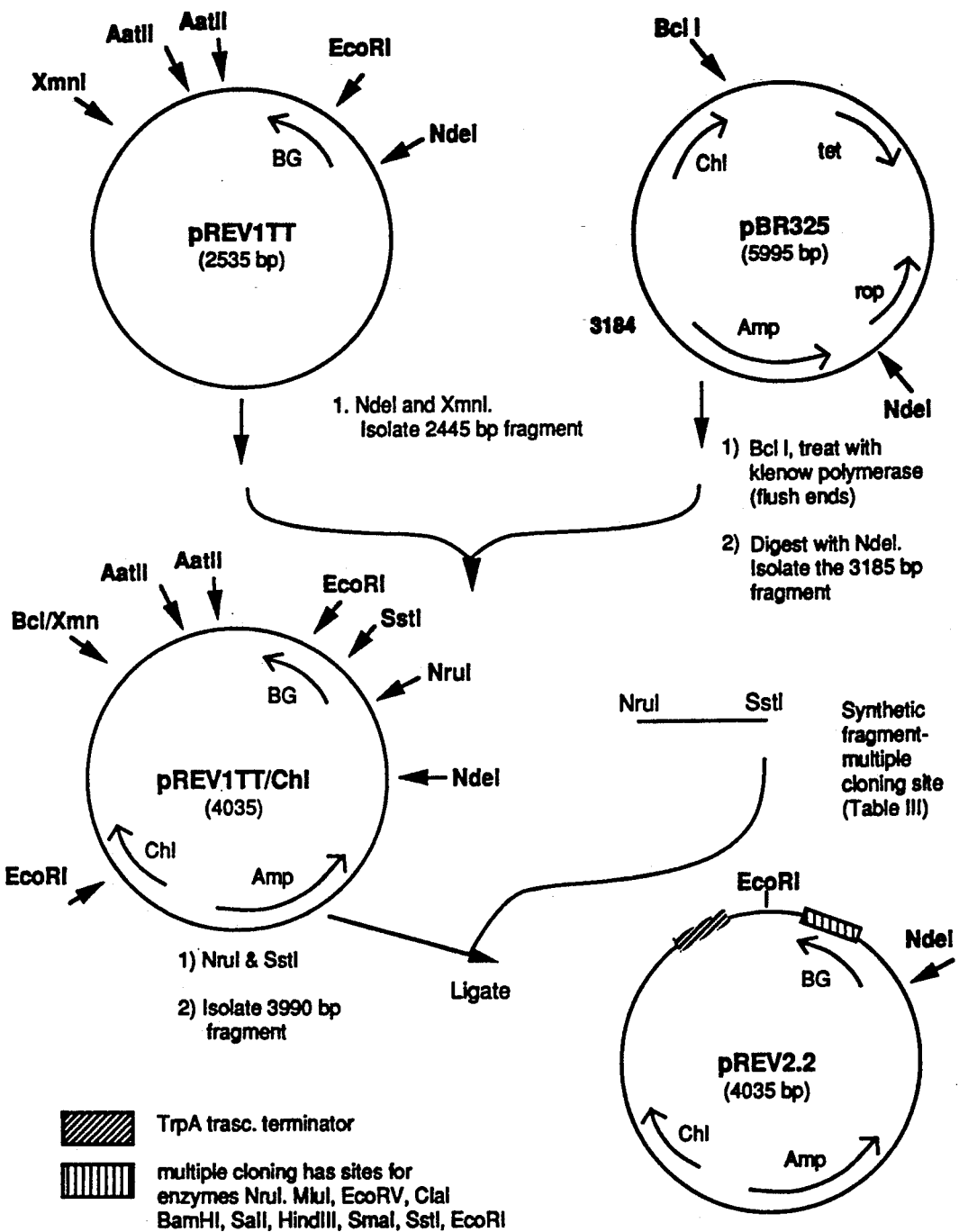

United States Patent [19]

Putney et al.

[11] Patent Number: 5,262,301
[45] Date of Patent: Nov. 16, 1993

[54] RECOMBINANT HTLV-III PROTEINS AND USES THEREOF

[75] Inventors: Scott D. Putney; Debra Lynn, both of Arlington; Kashayar Javaherian, Lexington; William T. Mueller, Watertown, all of Mass.; John Farley, Rochester, N.Y.

[73] Assignee: Repligen Corporation, Cambridge, Mass.

[21] Appl. No.: 817,025

[22] Filed: Jan. 3, 1992

Related U.S. Application Data

[60] Division of Ser. No. 588,514, Sep. 24, 1990, abandoned, which is a continuation-in-part of Ser. No. 892,680, Aug. 1, 1986, abandoned.

[51] Int. Cl.$^5$ .................... C12Q 1/70; C12Q 1/00; G01N 33/567; C07K 5/00
[52] U.S. Cl. .................... 435/5; 435/7.1; 422/56; 436/504; 530/350
[58] Field of Search .................... 435/7.1, 5; 422/56; 436/504

[56] References Cited

U.S. PATENT DOCUMENTS 4,520,113  5/1985  Gallo et al. .................... 436/504

OTHER PUBLICATIONS

Chang, et al., 1985, "Expression in *Escherichia coli* of Open . . . " Science 228: 93-96.
Crowl, et al., 1985, "HTLV-III Env Gene Products Synthesize of *E. coli* . . . " Cell 41: 979-986.

Primary Examiner—Christine M. Nucker
Assistant Examiner—Lynette F. Smith
Attorney, Agent, or Firm—Saliwanchik & Saliwanchik

[57] ABSTRACT

Novel recombinant HTLV-III fusion proteins denoted R10, RB1, 590 and the HIV portion of each of these proteins are useful in the diagnosis, prophylaxis or therapy of AIDS. Protein R10 is a 95 kD fusion protein; protein PB1 is a 26 kD fusion protein and protein 590 is an 86 kD fusion protein.

18 Claims, 12 Drawing Sheets

R10

PB1

590

KHI

▨ = E.Coli protein sequence

```
          Hinf1                                     Taq1
AGGAGTCCCTTATGTTACGTCCTGTAGAAACCCCAACCCGTGAAATCAAAAACTCGACGGC
                           Nru         ←—REV  env→
              CTGTGGGCATTCAGTCTGGATCGC......CATCTGAACCAATCTGTA......

Oligonucleotide
                AGGAGTCCCTTATGCTGAACCAATCTGTA
```

Figure 4

```
         env    REV
←——————————→ ←————
AACAATGAGTCCGAGATCCGTGGACAAGCTTCCCGGGAGCTCGAATTCTTGAAGACGAAAGGGCCT...
```

Oligonucleotide
AACAATGAGTCCGAGATCTGAAGACGAAAGGGCCTCGTG

Figure 5

Met
Val Trp Lys Glu Ala Thr Thr Leu Phe Cys Ala Ser Asp Ala Lys Ala Tyr
Asp Thr Glu Val His Asn Val Ala Thr Thr Ala Cys Val Pro Thr Asp Pro
Asn Pro Gln Val Leu Val Leu Asn Val Ile Asn Phe Asp Ala Met Trp Lys
Asn Asp Met Gln Gly Leu Met Ile Glu Thr Ala Phe Val Leu Trp Gln Ser
Leu Lys Pro Cys Lys Lys Leu Pro Leu Cys Val Ile Leu Lys Cys Gly Thr
Leu Lys Asn Asp Ala Thr Asn Ser Ser Val Gly Ser Ser Arg Ile Met Glu
Gly Glu Ile Lys Thr Ser Ser Asn Ser Ile Gly Arg Met Ile Gly Met Gly
Gln Lys Gly Tyr Ala Phe Phe Lys Asp Ile Ser Thr Ile Pro Ala Asp Lys
Thr Lys Tyr Tyr Phe Leu Pro Tyr Cys His Thr Val Ile Ile Gln Asn Val
Pro Ser Ser Phe Leu Thr Glu Pro His Asn Tyr Cys Ala Pro Thr Gln Ala
Ala Leu Lys Asn Gly Ile Lys Thr Gly Asn Gly Thr Val Ser Pro Cys Gly
Val Ser Val Gln Cys Thr His Gly Glu Phe Ile Arg Pro Val Ser Thr Asn
Leu Leu Asn Gly Ser Thr Ala Glu Ile Ile Arg Val Ile Ser Arg Ala Gln
Thr Asp Ala Ala Lys Thr Ile Ile Val Gln Ser Ala Asn Val Glu Ala Ile
Cys Thr Arg Pro Asn Thr Asn Asn Arg Lys Ser Ile Arg Ile Arg Gly His
Gly Arg Ala Phe Val Ile Gly Lys Ile Gly Asn Met Arg Gln Ala His Cys
Asn Ile Ser Arg Ala Lys Trp Asn Asn Thr Leu Gln Ile Asp Ser Lys Leu
Arg Glu Gln Phe Gly Asn Asn Lys Thr Ile Ile Phe Lys Gln Ser Ser Gly
Asp Pro Glu Ile Val Thr His Ser Phe Asn Cys Gly Gly Glu Phe Phe Tyr
Asn Ser Thr Trp Phe Asn Ser Thr Trp Ser Thr Glu Gly Ser Asn Thr Thr
Gly Asn Asn Thr Gly Leu Phe Asn Ser Thr Trp Ser Thr Glu Gly Arg Ile
Gln Ile Ile Asn Met Trp Gln Glu Val Gly Lys Ala Met Tyr Ala Pro Ile
Ser Gly Gln Ile Arg Cys Ser Ser Asn Ile Thr Gly Leu Leu Leu Thr Arg
Gly Gly Asn Ser Asn Asn Glu Ser Glu Ile Phe Arg Pro Gly Gly Gly Asp

Figure 6

```
ATGGTGTGGAAGGAAGCAACCACCACTCTATTTTGTGCATCAGATGCTAAAGCATAT
GATACAGAGGTACATAATGTTTGGGCCACACATGCCTGTGTACCCACAGACCCC
AACCCACAAGAAGTAGTATTGGTAAATGTGACAGAAAATTTAACATGTGAAA
AATGACACATGGTAGAACAGATGCATGAGGATATAATCAGTTTATGGATCAAAGC
CTAAAGCCATGTGTAAAATTAACCCCACTCTGTGTTAGTTTAAAGTGCACTGAT
TTGAAGAATGATATACTAATACCAATAGTAGTAGCGGGAGAATGATAATGGAGAAA
GGAGAGATAAAAAACTGCTCTTTCAATATCAGCACACAAGCATAAGAGGTAAGGTG
CAGAAAGAATATGCATTTTTTATAAACTTGATATATAACCAATAGATAATGAT
ACTACCAGCTATACGTTGACAAGTTGTAACACCTCAGTCATTACACAGGCCTGT
CCAAAGGTATCCTTTGAGCCAATTCCCATACATTATTGTGCCCCGGCTGTTTT
GCGATTCTAAAATGTAATAAGACGTTCAATGGAACAGGACCATGTACAAAT
GTCAGCACAGTACAATGTACACATGGAATTAGGCCAGTAGTAATCAACTCAACTG
CTGTTAAATGGCAGTCTGGCAGAAGAAGAGTAGTAATTAGATCTGCCAATTC
ACAGACAATGCTAAACCATAATAGTACAGCTGAACCAATCTGTAGAAATTAAT
TGTACAAGACCCAACAACAATAGTACAAGAAAAATAGTATCCGTATCCAGAGGACCA
GGGAGAGCATTGTTACAATAGCAAATGGAATAAAACATTTAAACAGATAGCAAATTA
AACATTAGTAGAGCAAATTTGGAATAATAAAACAATAATCTTAAGCAGTCCTCAGGAGG
AGAGAACAATTGTAACGCACAGTTTAATAGTACTTGGTTTAATAGTACTTGGAGTACTAAA
GACCCAGAAAATTGTAACGCACAGTTTAATAGTACTTGGTTTAATAGTACTTGGAGTACTAAA
AATTCAACACAACTGTTTAATAGTACTTGGTTTAATAGTACTTGGAGTACTAAA
GGGTCAAATAATAACACTGAAGGAAGTGACACAATCACCCTCCCATGCAGAATAAAA
CAAATTATAAACATGTGGCAGGAAGTAGGAAAAGCAATGTATGCCCCTCCCATC
AGTGGACAAATTAGATGTTCATCAAATATTACAGGGCTGCTATTAACAAGAGAT
GGTGGTAATAGCAACAATGAGTCC
```

Figure 7

```
Met Leu Asn Gln Ser Val Glu Ile Asn Cys Thr Arg Pro Asn Asn Thr Arg Lys
Ser Ile Arg Ile Gln Arg Gly Pro Gly Arg Ala Phe Val Thr Ile Gly Lys Ile
Gly Asn Met Arg Gln Ala His Cys Asn Ile Ser Arg Ala Lys Trp Asn Asn Thr
Leu Lys Gln Ile Asp Ser Lys Leu Arg Glu Gln Phe Gly Asn Lys Thr Ile
Ile Phe Lys Gln Ser Ser Gly Gly Asp Pro Glu Ile Val Thr His Ser Phe Asn
Cys Gly Gly Glu Phe Phe Tyr Cys Asn Ser Thr Gln Leu Phe Asn Ser Thr Trp
Phe Asn Ser Thr Trp Ser Thr Lys Gly Ser Asn Asn Thr Glu Gly Ser Asp Thr
Ile Thr Leu Pro Cys Arg Ile Lys Gln Ile Ile Asn Met Trp Gln Glu Val Gly
Lys Ala Met Tyr Ala Pro Pro Ile Ser Gly Gln Ile Arg Cys Ser Ser Asn Ile
Thr Gly Leu Leu Leu Thr Arg Asp Gly Gly Asn Ser Asn Asn Glu Ser
```

Figure 8

ATGCTGAACCAATCTGTAGAAATTAATTGTACAAGACCCAACAACAATACAAGAAAA
AGTATCCGTATCCAGAGAGGACCAGGAGAGCATTTGTTACAATAGGAAAAATA
GGAAATATGAGACAAGCACACATTGTAACATTAGTAGAGCAAAATGAATAACACT
TTAAACAGATAGATAGCACAATTAAGAGAACAATTTGGAAATAAAACAATA
ATCTTTAAGCAGTCCTCAGGAGGGACCCAGAAATTGTAACGCACAGTTTAAT
TGTGGAGGGGAATTTTTCTACTGTAATTCAACACAACTGTTTAATAGTACTTGG
TTTAATAGTACTTGGAGTACTAAAGGGTCAAATAACACTGAAGGAAGTGACACA
ATCACCCTCCCATGCAGAATAAAACAAATTATAAACATGTGGCAGGAAGTAGGA
AAAGCAATGTATGCCCCTCCCATCAGTGGACAAATTAGATGTTCATCAAATATT
ACAGGGCTGCTATTAACAAGAGATGGTGGTAATAGCAACAATGAGTCC

Figure 9

Met Leu Asn Gln Ser Val Glu Ile Asn Cys Thr Arg Pro Asn Asn Asn Thr Arg
Ser Ile Arg Ile Gln Arg Gly Pro Gly Arg Ala Phe Val Thr Ile Gly Lys Ile
Gly Asn Met Arg Gln Ala His Cys Asn Ile Ser Arg Ala Lys Trp Asn Asn Thr
Leu Lys Gln Ile Asp Ser Lys Leu Arg Glu Gln Phe Gly Asn Asn Lys Thr Ile
Ile Phe Lys Gln Ser Ser Gly Gly Asp Pro Glu Ile Val Thr His Ser Phe Asn
Cys Gly Gly Glu Phe Phe Tyr Cys Asn Ser Thr Gln Leu Phe Asn Ser Thr Trp
Phe Asn Ser Thr Trp Ser Thr Lys Gly Ser Asn Asn Thr Glu Gly Ser Asp Thr
Ile Thr Leu Pro Cys Arg Ile Lys Gln Ile Ile Asn Met Trp Gln Glu Val Gly
Lys Ala Met Tyr Ala Pro Pro Ile Ser Gly Gln Ile Arg Cys Ser Ser Asn Ile
Thr Gly Leu Leu Leu Thr Arg Asp Gly Gly Asn Ser Asn Asn Glu Ser Glu Ile
Phe Arg Pro Gly Gly Gly Asp Met Arg Asp Asn Trp Arg Ser Glu Leu Tyr Lys
Tyr Lys Val Val Lys Ile Glu Pro Leu Gly Val Ala Pro Thr Lys Ala Lys Arg
Arg Val Val Gln Arg Glu Lys Arg Ala Val Gly Ile Gly Ala Leu Phe Leu Gly
Phe Leu Gly Ala Ala Gly Ser Thr Met Gly Ala Ala Ser Met Thr Leu Thr Val
Gln Ala Arg Gln Leu Leu Ser Gly Ile Val Gln Gln Gln Asn Asn Leu Leu Arg
Ala Ile Glu Ala Gln Gln His Leu Leu Gln Leu Thr Val Trp Gly Ile Lys Gln
Leu Gln Ala Arg Ile Leu Ala Val Glu Arg Tyr Leu Lys Asp Gln Gln Leu Leu
Gly Ile Trp Gly Cys Ser Gly Lys Leu Ile Cys Thr Thr Ala Val Pro Trp Asn
Ala Ser Trp Ser Asn Lys Ser Leu Glu Gln Ile Trp Asn Asn Met Thr Trp Met
Glu Trp Asp Arg Glu Ile Asn Asn Tyr Thr

Figure 10

```
ATGCTGAACCAATCTGTAGAAATTAATTGTACAAGACCCAACAACAATACAAGAAAA
AGTATCCGTATCCAGAGAGCAAGAGGACCAGGAGAGCATTGTTACAATAGGAAAAATA
GGAAATATGAGACAAGCACATTGTAACATTAGTAGAGCAAAATGGAATAACACT
TTAAAACAGATAGATAGCAAATTAAGAGAACAAATTGGAATATAAAACAATA
ATCTTTAAGCAGTCCTCAGGAGGGACCCAGAAATTGTAACGCCACAGTTTAAT
TGTGGAGGGGAATTTTTCTACTGTAATTCAACACAACTGTTAATAGTACTTGG
TTTAATAGTACTTGGAGTACTAAAGGGTCAAATAACACTGAAGGAAGTGACACA
ATCACCCTCCCATGCAGAATAAAACAAATTATAAACATGTGGCAGGAAGTAGGA
AAAGCAATGTATGCCCCTCCCATCAGTGGACAAATTAGATGTTCATCAAATATT
ACAGGGCTGCTATTAACAAGAGATGGTGGTAATAGCAACAATGAGTCCGAGATC
TTCAGACCTGGAGGAGGAGATATGAGGGACAATTGGAGAAGTGAATTATATAAA
TATAAAGTAGTAAAATTGAACCATTAGGAGTAGCACCCACCAAGGCAAAGAGA
AGAGTGGTGCAGAGAGAAAAAGAGCACTAGTGGGCGCAGCGTCAATGACGCTGACGGTA
TTCTTGGGAGCAGCAGGAAGCACTATGGGCGCAGCGTCAATGACGCTGACGGTA
CAGGCCAGACAATTATTGTCTGGTATAGTGCAGCAGCAGAACAATTTGCTGAGG
GCTATTGAGGCGCAACAGCATCTGTTGCAACTCACAGTCTGGGCATCAAGCAG
CTCCAGGCAAGAATCCTGGCTCTGGAAAGATACCTAAAGGATCAACAGCTCCTG
GGGATTTGGGGTTGCTCTGGAAAACTCATTTGCACCACTGCTGTGCCTTGAAT
GCTAGTTGGAGTAATAATCTCTGAACAGATTTGGAATAACATGACCTGGATG
GAGTGGGACAGAGAAATTAACAATTACACA
```

Figure 11

RECOMBINANT HTLV-III PROTEINS AND USES THEREOF

This is a division of application Ser. No. 07/588,514, filed Sep. 24, 1990, now abandoned, which is a continuation-in-part of copending application Ser. No. 892,680, filed Aug. 1, 1986 now abandoned.

BACKGROUND OF THE INVENTION

Human T-cell lymphotropic virus (HTLV-III), lymphadenopathy-associated virus (LAV), or AIDS-associated retrovirus (ARV) has been identified as the cause of acquired immune deficiency syndrome (AIDS) (Popovic, M., Sarngadharan, M. G., Read, E. and Gallo, R. C., [1984] Science 224:497–500). The virus displays tropism for the OKTr+lymphocyte subset (Klatzmann, D., Barre-Sinoussi, F., Nugeyre, M. T., Dauguet, C., Vilmer, E., Griscelli, C., Brun-Vezinet, F., Rouzioux, C., Gluckman, J. C., Chermann, J. C. and Montagnier, L. [1984] Science 225:59–63). Antibodies against HTLV-III proteins in the sera of most AIDS and AIDS related complex (ARC) patients, and in asymptomatic people infected with the virus (Sarngadharan, M. G., Popovic, M., Bruch, L., Schupbach, J. and Gallo, R. C. [1984] Science 224:506–508) have made possible the development of immunologically based tests that detect antibodies to these antigens. These tests are used to limit the spread of HTLV-III through blood transfusion by identifying blood samples of people infected with the virus. Diagnostic tests currently available commercially use the proteins of inactivated virus as antigens.

In addition to allowing new approaches for diagnosis, recombinant DNA holds great promise for the development of vaccines against both bacteria and viruses (Wilson, T. [1984] Bio/Technology 2:29–39). The most widely employed organisms to express recombinant vaccines have been *E. coli, S. cerevisiae* and cultured mammalian cells. For example, subunit vaccines against foot and mouth disease (Kleid, D. G., Yansura, D., Small, B., Dowbenko, D., Moore, D. M., Brubman, M. J., McKercher, P. D., Morgan, D. O., Robertson, B. H. and Bachrach, H. L. [1981] Science 214:1125–1129) and malaria (Young, J. F., Hockmeyer, W. T., Gross, M., Ripley Ballou, W., Wirtz, R. A., Trosper, J. H., Beudoin, R. L., Hollingdale, M. R., Miller, L. M., Diggs, C. L. and Rosenberg, M. [1985]Science 228:958–962) have been synthesized in *E. coli*. Other examples are hepatitis B surface antigen produced in yeast (McAleer, W. J., Buynak, E. B., Maigetter, R. Z., Wampler, D. E., Miller, W. J. and Hilleman, M. R. [1984]Nature 307:178–180) and a herpes vaccine produced in mammalian cells (Berman, P. W., Gregory, T., Chase, D. and Lasky, L. A. [1984] Science 227:1490–1492).

There is a real need at this time to develop a vaccine for AIDS. No such vaccine is known to exist.

BRIEF SUMMARY OF THE INVENTION

The subject invention concerns novel recombinant HTLV-III proteins and the uses thereof. More specifically, the subject invention concerns novel recombinant HTLV-III envelope proteins which can be used in the diagnosis, prophylaxis or therapy of AIDS. These novel proteins are encoded on bacterial plasmids which can be used to transform suitable hosts, for example, *E. coli*, using standard procedures.

REFERENCE TO THE DRAWINGS

FIG. 1—This is a flow chart of the construction of plasmid pREV2.2 which is used to construct vectors encoding novel proteins.

Figure 2:
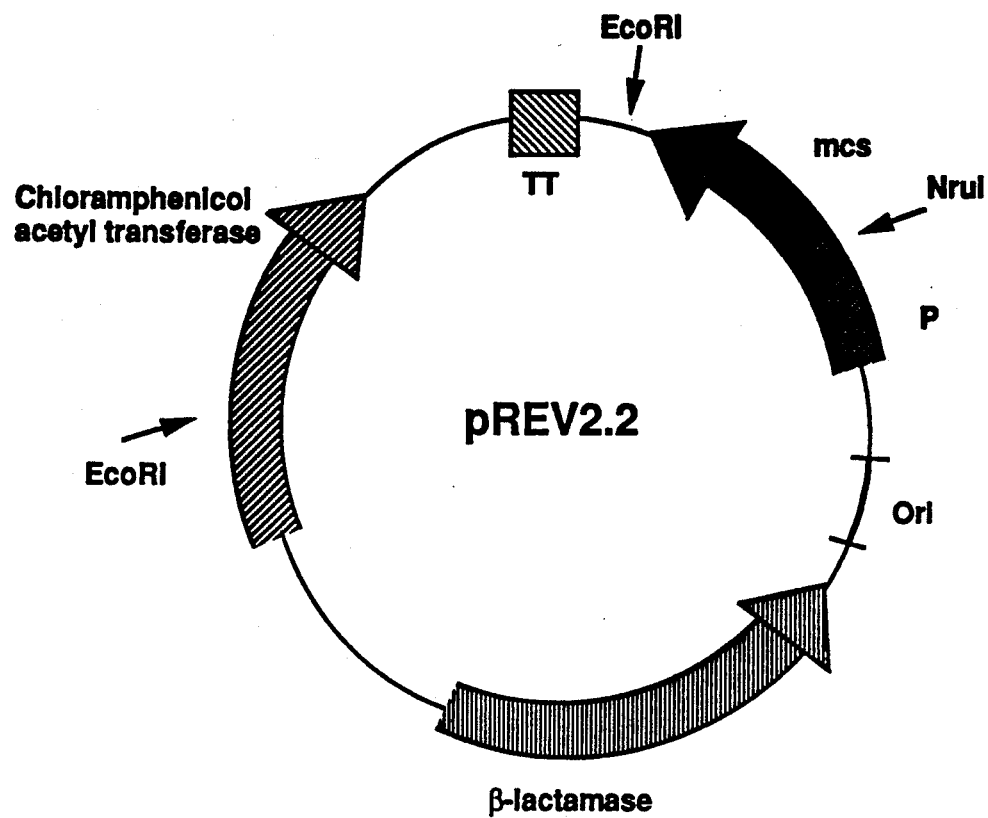
Figure 2:
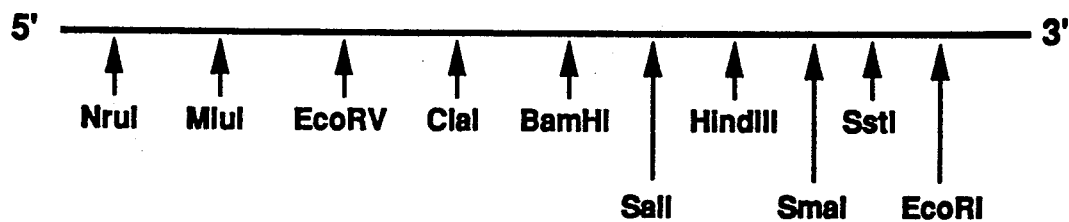

FIG. 2—This is a diagram of plasmid pREV2.2 showing the multiple cloning site.

Figure 3:
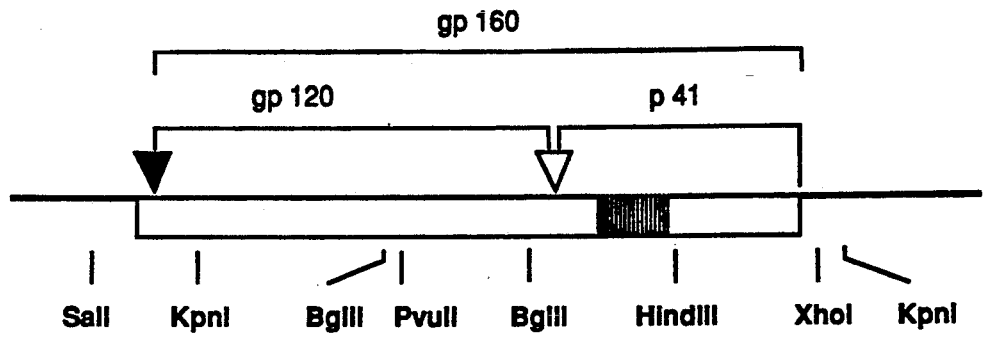
Figure 3:
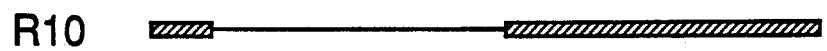
Figure 3:
Figure 3:
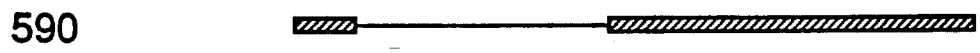
Figure 3:

FIG. 3—This is a schematic of the HTLV-III envelope gene and the novel recombinant proteins obtained therefrom.

FIG. 4—Drawing showing the removal of N-terminal non-HTLV-III sequences of PB1.

FIG. 5—Drawing showing the removal of C-terminal non-HTLV-III sequences from PB1.

FIG. 6—The amino acid sequenceof the HIV portion of protein R10.

FIG. 7—The nucleotide sequence encoding the HIV portion of protein R10.

FIG. 8—The amino acid sequence of the HIV portion of protein PB1.

FIG. 9—The nucleotide sequence encoding the HIV portion of protein PB1.

FIG. 10—The amino acid sequence of the HIV portion of protein 590.

FIG. 11—The nucleotide sequence encoding the HIV portion of protein 590.

DETAILED DISCLOSURE OF THE INVENTION

Expression vector plasmid pREV2.2 was constructed from plasmid pBG1. The flow chart showing the construction of this plasmid is given in FIG. 1 of the drawings.

Plasmid pR10 contains approximately 1275 base pairs of DNA encoding the HTLV-III env gene from essentially the KpnI site to the BglII site. This plasmid in a suitable bacterial host, e.g., *E. coli*, can be used to produce the novel recombinant HTLV-III 95 kD fusion protein denoted R10. The amino acid sequence of fusion protein R10 is shown in Table 8; the DNA sequence encoding this protein is shown in Table 8A. The amino acid sequence of the HIV portion of protein R10 is shown in FIG. 6. The DNA sequence encoding the HIV portion of protein R10 is shown in FIG. 7.

Plasmid pPB1 contains approximately 540 base pairs of DNA encoding essentially the HTLV-III env gene from the PvuII site tot he BGIII site. This plasmid in a suitable host, e.g., *E. coli*, can be used to produce the novel recombinant HTLV-III 26 kD fusion protein denoted PB1. The amino acid sequence of fusion protein PB1 is shown in Table 9; the DNA sequence encoding this protein is shown in Table 9A. The amino acid sequence of the HIV portion of protein PB1 is shown in FIG. 8. The DNA sequence encoding the HIV portion of protein PB1 is shown in FIG. 9.

Plasmid p590 contains approximately 1055 base pairs of DNA encoding essentially the HTLV-III env gene from the PvuII site to the HindII site. This plasmid in a suitable host, e.g., *E. coli*, can be used to produce the novel recombinant HTLV-III 86 kD protein denoted 590. The amino acid sequence of fusion protein 590 is shown in Table 10; the DNA sequence encoding this protein is shown in Table 10A. The amino acid sequence of the HIV portion of protein 590 is shown in FIG. 10. The DNA sequence encoding the HIV portion of protein 590 is shown in FIG. 11.

Plasmid pKH1 contains approximately 1830 base pairs of DNA encoding essentially the HTLV-III env gene from the KpnI site to the HindIII site. This plasmid in a suitable host, e.g., *E. coli*, can be used to produce the novel recombinant HTLV-III 70 kD protein denoted KH1. The amino acid sequence of fusion protein KH1 is shown in Table 11; the DNA sequence encoding this protein is shown in Table 11A. The amino acid sequence of the HIV portion of protein KH1 is shown in Table 12. The DNA sequence encoding the HIV portion of protein KH1 is shown in Table 12A.

Plasmid pBG1 is deposited in the *E. coli* host MS371 with the Northern Regional Research Laboratory (NRRL), U.S. Department of Agriculture, Peoria, Ill. USA. It is in the permanent collection of this repository. *E. coli* MS371 (pBGl), NRRL B-15904, was deposited on Nov. 1, 1984. *E. coli* MS371, NRRL B-15129 is now available to the public. *E. coil* SG20251, NRRL B-15918, was deposited on Dec. 12, 1984. NRRL B-15904 and NRRL B-15918 will be available to the public upon the grant of a patent which discloses them. Other cultures which were deposited with NRRL and their deposit dates and numbers are as follows:

| Culture | Repository No. | Date of Deposit |
|---|---|---|
| *E. coli* JM103(pREV2.2) | NRRL B-18091 | July 30, 1986 |
| *E. coli* SG20251(pR10) | NRRL B-18093 | July 30, 1986 |
| *E. coli* SG20251(pPB1) | NRRL B-18092 | July 30, 1986 |
| *E. coli* SG20251(p590) | NRRL B-18094 | July 30, 1986 |
| *E. coli* CAG629(pKH1) | NRRL B-18095 | July 30, 1986 |

The above deposits will be maintained in the NRRL repository for at least 30 years and will be made available to the public upon the grant of a patent disclosing them. The deposits are also available as required by foreign patent laws in countries wherein counterparts of the subject application, or its progeny, are filed. However, it should be understood that the availability of a deposit does not constituted a license to practice the subject invention in derogation of patent rights granted by governmental action.

The novel HTLV-III proteins of the subject invention can be expressed in *Saccharomyces cerevisiae* using plasmids containing the inducible galactose promoter from this organism (Broach, J. R., Li, Y., Wu, L. C. and Jayaram, M. in Experimental Manipulation of Gene Expression [1983] p. 83, ed., M. Inouye, Academic Press). These plasmids are called YEp51 and YEp52 (Broach, J. R. et al. [1983]) and contain the *E. coli* origin of replication, the gene for β-lactamase, the yeast LEU2 gene, the 2 μm origin of replication and the 2 μm circle REP3 locus. Recombinant gene expression is driven by the yeast GAL10 gene promoter.

Yeast promoters such as galactose and alcohol dehydrogenase (Bennetzen, J. L. and Hall, B. D. [1982] J. Biol. Chem. 257:3018; Ammerer, G. in Methods in Enzymology [1983] Vol. 101, p. 192), phosphoglycerate kinase (Derynck, R., Hitzeman, R. A., Gray, P. W., Goeddel, D. V., in Experimental Manipulation of Gene Expression [1983] p. 247, ed. M. Inouye, Academic Press), triose phosphate isomerase (Alber, T. and Kawasaki, G. [1982] J. Molec. and Applied Genet. 1:419), or enolase (Innes, M. A. et al. [1985] Science 226:21) can be used.

The genes disclosed herein can be expressed in simian cells. When the genes encoding these proteins are cloned into one of the plasmids as described in Okayama and Berg (Okayama, H. and Berg, P. [1983] Molec. and Cell. Biol. 3:280) and references therein, or COS cells transformed with these plasmids, synthesis of HTLV-III proteins can be detected immunologically.

Other mammalian cell gene expression/protein production systems can be used. Examples of other such systems are the vaccinia virus expression system (Moss. B. [1985] Immunology Today 6:243; Chakrabarti, S., Brechling, K., Moss, B. [1985]Molec. and Cell. Biol. 5:3403) and the vectors derived from murine retroviruses (Mulligan, R. C. in Experimental Manipulation of Gene Expression [1983] p. 155, ed. M. Inouye, Academic Press).

The HTLV-III proteins of the subject invention can be chemically synthesized by solid phase peptide synthetic techniques such as BOC and FMOS (Merrifield, R. B. [1963] J. Amer. Chem. Soc. 85:2149; Chang, C. and Meienhofer, J. [1978] Int. J. Peptide Protein Res. 11:246).

As is well known in the art, the amino acid sequence of a protein is determined by the nucleotide sequence of the DNA. Because of the redundancy of the genetic code, i.e., more than one coding nucleotide triplet (codon) can be used for most of the amino acids used to make proteins, different nucleotide sequences can code for a particular amino acid. Thus, the genetic code can be depicted as follows:

| | | | |
|---|---|---|---|
| Phenylalanine (Phe) | TTK | Histidine (His) | CAK |
| Leucine (Leu) | XTY | Glutamine (Gln) | CAJ |
| Isoleucine (Ile) | ATM | Asparagine (Asn) | AAK |
| Methionine (Met) | ATG | Lysine (Lys) | AAJ |
| Valine (Val) | GTL | Aspartic acid (Asp) | GAK |
| Serine (Ser) | QRS | Glutamic acid (Glu) | CAJ |
| Proline (Pro) | CCL | Cysteine (Cys) | TGK |
| Threonine (Thr) | ACL | Tryptophan (Trp) | TGG |
| Alanine (Ala) | GCL | Arginine (Arg) | WGZ |
| Tyrosine (Tyr) | TAK | Glycine (Gly) | GGL |
| Termination Signal | TAJ | | |
| Termination Signal | TGA | | |

Key: Each 3-letter deoxynucleotide triplet corresponds to a trinucleotide of mRNA, having a 5′-end on the left and a 3′-end on the right. All DNA sequences given herein are those of the strand whose sequence corresponds to the mRNA sequence, with thymine substituted for uracil. The letters stand for the purine or pyrimidine bases forming the deoxynucleotide sequence.

A=adenine
G=guanine
C=cytosine
T=thymine
X=T or C if Y is A or G
X=C if Y is C or T
Y=A, G, C or T if X is C
Y=A or G if X is T
W=C or A if Z is A or G
W=C if Z is C or T
Z=A, G, C or T if W is C
Z=A or G if W is A
QR=TC if S is A, G, C or T; alternatively QR=AG if S is T or C
J=A or G
K=T or C
L=A, T, C or G
M=A, C or T The above shows that the novel amino acid sequences of the HTLV-III proteins of the subject invention can be prepared by nucleotide sequences other than those disclosed herein. Functionally equivalent nucleotide sequences encoding the novel amino acid sequences of these HTLV-III proteins, or fragments thereof having HTLV-III antigenic or immunogenic or therapeutic activity, can be prepared by known synthetic procedures. Accordingly, the subject invention includes such functionally equivalent nucleotide sequences.

Thus the scope of the subject invention includes not only the specific nucleotide sequences depicted herein, but also all equivalent nucleotide sequences coding for molecules with substantially the same HTLV-III antigenic or immunogenic or therapeutic activity.

Further, the scope of the subject invention is intended to cover not only the specific amino acid sequences disclosed, but also similar sequences coding for proteins or protein fragments having comparable ability to induce the formation of and/or bind to specific HTLV-III antibodies.

The term "equivalent" is being used in its ordinary patent usage here as denoting a nucleotide sequence which performs substantially as the nucleotide sequence identified herein to produce molecules with substantially the same HTLV-III antigenic or immunogenic or therapeutic activity in essentially the same kind of hosts. Within this definition are subfragments which have HTLV-III antigenic or immunogenic or therapeutic activity.

As disclosed above, it is well within the skill of those in the genetic engineering art to use the nucleotide sequences encoding HTLV-III antigenic or immunogenic or therapeutic activity of the subject invention to produce HTLV-III proteins via microbial processes. Fusing the sequences into an expression vector and transforming or transfecting into hosts, either eukaryotic (yeast or mammalian cells) or prokaryotic (bacterial cells), are standard procedures used in producing other well-known proteins, e.g., insulin, interferons, human growth hormone, IL-1, IL-2, and the like. Similar procedures, or obvious modifications thereof, can be employed to prepare HTLV-III proteins by microbial means or tissue-culture technology in accord with the subject invention.

The nucleotide sequences disclosed herein can be prepared by a "gene machine" by procedures well known in the art. This is possible because of the disclosure of the nucleotide sequence.

The restriction enzymes disclosed can be purchased from Bethesda Research Laboratories, Gaithersburg, Md., or New England Biolabs, Beverly, Mass. The enzymes are used according to the instructions provided by the supplier.

The various methods employed in the preparation of the plasmids and transformation of host organisms are well known in the art. These procedures are all described in Maniatis, T., Fritsch, E. F., and Sambrook, J. (1982) *Molecular Cloning: A Laboratory Manual,* Cold Spring Harbor Laboratory, New York. Thus, it is within the skill of those in the genetic engineering art to extract DNA from microbial cells, perform restriction enzyme digestions, electrophorese DNA fragments, tail and anneal plasmid and insert DNA, ligate DNA, transform cells, e.g., *E. coli* cells, prepare plasmid DNA, electrophorese proteins, and sequence DNA.

Immunochemical assays employing the HTLV-III proteins of the invention can take a variety of forms. The preferred type is a solid phase immunometric assay. In assays of this type, an HTLV-III protein is immobilized on a solid phase to form an antigen-immunoadsorbent. The immunoadsorbent is incubated with the sample to be tested. After an appropriate incubation period, the immunoadsorbent is separated from the sample and labeled anti-(human IgG) antibody is used to detect human anti-HTLV-III antibody bound to the immunoadsorbent. The amount of label associated with the immunoadsorbent can be compared to positive and negative controls to assess the presence or absence of anti-HTLV-III antibody.

The immunoadsorbent can be prepared by adsorbing or coupling a purified HTLV-III protein to a solid phase. Various solid phases can be used, such as beads formed of glass, polystyrene, polypropylene, dextran or other material. Other suitable solid phases include tubes or plates formed from or coated with these materials.

The HTLV-III proteins can be either covalently or non-covalently bound to the solid phase by techniques such as covalent bonding via an amide or ester linkage or adsorption. After the HTLV-III protein is affixed to the solid phase, the solid phase can be post-coated with an animal protein, e.g., 3% fish gelatin. This provides a blocking protein which reduces nonspecific adsorption of protein to the immunoadsorbent surface.

The immunoadsorbent is then incubated with the sample to be test for anti-HTLV-III antibody. In blood screening, blood plasma or serum is used. The plasma or serum is diluted with normal animal plasma or serum. The diluene plasma or serum is derived from the same animal species that is the source of the anti-(human IgG) antibody. The preferred anti-(human IgG) antibody is goat anti-(human IgG) antibody. Thus, in the preferred format, the diluent would be goat serum or plasma.

The conditions of incubation, e.g., pH and temperature, and the duration of incubation are not crucial. These parameters can be optimized by routine experimentation. Generally, the incubation will be run for 1-2 hr at about 45° C. in a buffer of pH 7-8.

After incubation, the immunoadsorbent and the sample are separated. Separation can be accomplished by any conventional separation technique such as sedimentation or centrifugation. The immunoadsorbent then may be washed free of sample to eliminate any interfering substances.

The immunoadsorbent is incubated with the labeled anti-(human IgG) antibody (tracer) to detect human antibody bound thereto. Generally the immunoadsorbent is incubated with a solution of the labeled anti-(human IgG) antibody which contains a small amount (about 1%) of the serum or plasma of the animal species which serves as the source of the anti-(human IgG) antibody. Anti-(human IgG) antibody can be obtained from any animal source. However, goat anti-(human IgG) antibody is preferred. The anti-(human IgG) antibody can be an antibody against the Fc Fragment of human IgG, for example, goat anti-(human IgG) Fc antibody.

The anti-(human IgG) antibody or anti-(human IgG)Fc can be labeled with a radioactive material such as $^{125}$ iodine; labeled with an optical label, such as a fluorescent material; or labeled with an enzyme such as horseradish peroxidase. The anti-human antibody can also be biotinylated and labeled avidin used to detect its binding to the immunoadsorbent.

After incubation with the labeled antibody, the immunoadsorbent is separated from the solution and the label associated with the immunoadsorbent is evaluated. Depending upon the choice of label, the evaluation can be done in a variety of ways. The label may be detected by a gamma counter if the label is a radioactive gamma emitter, or by a fluorimeter, if the label is a fluorescent material. In the case of an enzyme, label detection may be done colorimetrically employing a substrate for the enzyme.

The amount of label associated with the immunoadsorbent is compared with positive and negative controls in order to determine the presence of anti-HTLV-III antibody. The controls are generally run concomitantly with the sample to be tested. A positive control is a serum containing antibody against HTLV-III; a negative control is a serum from healthy individuals which does not contain antibody against HTLV-III.

For convenience and standardization, reagents for the performance of the immunometric assay can be assembled in assay kits. A kit for screening blood, for example, can include:

(a) an immunoadsorbent, e.g., a polystyrene bead coated with an HTLV-III protein;
(b) a diluent for the serum or plasma sample, e.g., normal goat serum or plasma;
(c) an anti-(human IgG) antibody, e.g., goat anti-(human IgG) antibody in buffered, aqueous solution containing about 1% goat serum or plasma;
(d) a positive control, e.g., serum containing antibody against at least one of the novel HTLV-III proteins; and
(e) a negative control, e.g., pooled sera from healthy individuals which does not contain antibody against at least one of the novel HTLV-III proteins.

If the label is an enzyme, an additional element of the kit can be the substrate for the enzyme.

Another type of assay for anti-HTLV-III antibody is an antigen sandwich assay. In this assay, a labeled HTLV-III protein is used in place of anti-(human IgG) antibody to detect anti-HTLV-III antibody bound to the immunoadsorbent. The assay is based in principle on the bivalency of antibody molecules. One binding site of the antibody binds the antigen affixed to the solid phase; the second is available for binding the labeled antigen. The assay procedure is essentially the same as described for the immunometric assay except that after incubation with the sample, the immunoadsorbent is incubated with a solution of labeled HTLV-III protein. HTLV-III proteins can be labeled with radioisotope, an enzyme, etc. for this type of assay.

In a third format, the bacterial protein, protein A, which binds the Fc segment of an IgG molecule without interfering with the antigen-antibody interaction can be used as the labeled tracer to detect anti-HTLV- antibody adsorbed to the immunoadsorbent. Protein A can be readily labeled with a radioisotope, enzyme or other detectable species.

Immunochemical assays employing an HTLV-III protein have several advantages over those employing a whole (or disrupted) virus. Assays based upon an HTLV-III protein will alleviate the concern over growing large quantities of infectious virus and the inherent variability associated with cell culturing and virus production. Further, the assay will help mitigate the real or perceived fear of contracting AIDS by technicians in hospitals, clinics and blood banks who perform the test.

Vaccines comprising one or more of the HTLV-III proteins, disclosed herein, and variants thereof having antigenic properties, can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants, such as aluminum hydroxide or muramyl dipeptide, which enhance the effectiveness of the vaccine. The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of manitol, lactose, starch, magnesium stearate, sodium saccharine, cellulose, magnesium carbonate and the like. These compositions can take the form of solutions, suspensions, tablets, pills, capsules, sustained release formulations or powders and contain from about 10% to about 95% of active ingredient, preferably from about 25% to about 70%.

The proteins can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, capacity of the subject's immune system to synthesize antibodies, and the degree of protection desired. Precise amounts of active ingredient required to be administered depend on the judgment of the practitioner and are peculiar to each individual. However, suitable dosage ranges are of the order of about several hundred micrograms active ingredient per individual. Suitable regimes for initial administration and booster shots are also variable, but are typified by an initial administration followed in one or two weeks intervals by a subsequent injection or other administration.

HTLV-III is known to undergo amino acid sequence variation, particularly in the envelope gene (Starcich, B. R. [1986] Cell 45:637–648; Hahn, B. H. et al. [1986] Science 232:1548–1553). Over 100 variants have been analyzed by molecular cloning and restriction enzyme recognition analysis, and several of these have been analyzed by nucleotide sequencing. Some of these are the HTLV-III isolates known as RF (Popovic, M. et al. [1984] Science 224:497–500), WMJ-1 (Hahn, B. H. et al. [1986] Science 232:1548–1553), LAV (Wain-Hobson, S.

et al. [1985] Cell 40:9–17), and ARV-2 (Sanchez-Pescador, R. et al. [1985] Science 227:484–492). Although the subject invention describes the sequence from one HTLV-III isolate, the appropriate envelope regions of any HTLV-III isolate can be produced using the procedures described herein for preparing R10, PB1, 590, and KH1. The HTLV-III proteins from different viral isolates can be used in vaccine preparations, as disclosed above, to protect against infections by different HTLV-III isolates. Further, a vaccine preparation can be made using more than one recombinant antigenic protein from more than one HTLV-III isolate to provide immunity and thus give better protection against AIDS.

Following are examples which illustrate the process of the invention, including the best mode. These examples should not be construed as limiting. All solvent mixture proportions are by volume unless otherwise noted.

Example 1—Construction of plasmid pREV2.2

The pREV2.2 plasmid expression vector was constructed from plasmid pBG1. Plasmid pBG1 can be isolated from its *E. coli* host by well known procedures, e.g., using cleared lysate-isopycnic density gradient procedures, and the like. Like pBG1, pREV2.2 expresses inserted genes behind the *E. coli* promoter. The differences between pBG1 and pREV2.2 are the following:

1. pREV2.2 lacks a functional replication of plasmid (rop) protein.
2. pREV2.2 has the trpA transcription terminator inserted into the AatII site. This sequence insures transcription termination of overexpressed genes.
3. pREV2.2 has genes to provide resistance to ampicillin and chloramphenicol, whereas pBG1 provides resistance only to ampicillin.
4. pREV2.2 contains a sequence encoding sites for several restriction endonucleases.

The following procedures, shown in FIG. 1 of the drawings, were used to make each of the four changes listed above:

1a. 5 $\mu$g of plasmid pBG1 was restricted with NdeI which gives two fragments of approximately 2160 and 3440 base pairs.

1b. 0.1 $\mu$g of DNA from the digestion mixture, after inactivation of the NdeI, was treated with T4 DNA ligase under conditions that favor intramolecular ligation (200 $\mu$l reaction volume using standard T4 ligase reaction conditions [New England Biolabs, Beverly, Mass]). Intramolecular ligation of the 3440 base pair fragment gave an ampicillin resistant plasmid. The ligation mixture was transformed into the recipient strain *E. coli* JM103 (available from New England Biolabs) and ampicillin resistant clones were selected by standard procedures.

1c. The product plasmid, pBG1$\Delta$N, where the 2160 base pair NdeI fragment is deleted from pBG1, was selected by preparing plasmid from ampicillin resistant clones and determining the restriction digestion patterns with NdeI and SalI (product fragments approximately 1790 and 1650). This declaration inactivities the rop gene that controls plasmid replication.

2a. 5 $\mu$g of pBG1$\Delta$N was then digested with EcoRI and BclI and the larger fragment, approximately 2455 base pairs, was isolated.

2b. A synthetic double stranded fragment was prepared by the procedure of Itakura et al. (Itakura, K., Rossi, J. J. and Wallace, R. B. [1984] Ann. Rev. Biochem. 53:323–356, and references therein) with the structure shown in Table 1. This fragment has BclI and EcoRI sticky ends and contains recognition sequences for several restriction endonucleases.

2c. 0.1 $\mu$g of the 2455 base pair EcoRI-BclI fragment and 0.01 $\mu$g of the synthetic fragment were joined with T4DNA ligase and competent cells of strain JM103 were transformed. Cells harboring the recombinant plasmid, where the synthetic fragment was inserted into pBG1$\Delta$N between the BclI and EcoRI sites, were selected by digestion of the plasmid with HpaI and EcoRI. The diagnostic fragment sizes are approximately 2355 and 200 base pairs. This plasmid is called pREV1.

2d. 5 $\mu$g of pREV1 were digested with AatII, which cleaves uniquely.

2e. The double stranded fragment shown in Table 2 was synthesized. This fragment has AatII sticky ends and contains the trpA transcription termination sequence.

2f. 0.1 $\mu$g of AatII digested pREV1 was ligated with 0.01 $\mu$g of the synthetic fragment in a volume of 20 $\mu$l using T4 DNA ligase.

2g. Cells of strain JM103, made competent, were transformed and ampicillin resistant clones selected.

2h. Using a KpnI, EcoRI double restriction digest of plasmid isolated from selected colonies, a cell containing the correct construction was isolated. The sizes of the KpnI, EcoRI generated fragments are approximately 2475 and 80 base pairs. This plasmid is called pREV1TT and contains the trpA transcription terminator.

3a. 5 $\mu$g of pREV1TT, prepared as disclosed above (by standard methods) was cleaved with NdeI and XmnI and the approximately 850 base pair fragment was isolated.

3b. 5 $\mu$g of plasmid pBR325 (BRL, Gaithersburg, Md.), which contains the genes conferring resistance to chloramphenicol as well as to ampicillin and tetracycline, was cleaved with BclI and the ends blunted with Klenow polymerase and deoxynucleotides. After inactivating the enzyme, the mixture was treated with NdeI and the approximately 3185 base pair fragment was isolated. This fragment contains the genes for chloramphenicol and ampicillin resistance and the origin of replication.

3c. 0.1 $\mu$g of the NdeI-XmnI fragment from pREV1TT and the NdeI-BclI fragment from pBR325 were ligated in 20 $\mu$l with T4 DNA ligase and the mixture used to transform competent cells of strain JM103. Cells resistant to both ampicillin and chloramphenicol were selected.

3d. Using an EcoRI and NdeI double digest of plasmid from selected clones, a plasmid was selected giving fragment sizes of approximately 2480, 1145, and 410 base pairs. This is called plasmid pREV1TT/ch1 and has genes for resistance to both ampicillin and chloramphenicol.

4a. A double stranded fragment shown in Table 3 was synthesized. This fragment, with a blunt end and an SstI sticky end, contains recognition sequences for several restriction enzyme sites.

4b. 5 μg of pREV1TT/ch1 was cleaved with NruI (which cleaves about 20 nucleotides from the BclI site) and SstI (which cleaves within the multiple cloning site). The larger fragment, approximately 3990 base pairs, was isolated from an agarose gel.

4c. 0.1 μg of the NruI-SstI fragment from pREV1TT/ch1 and 0.01 μg of the synthetic fragment were treated with T4 DNA ligase in a volume of 20 μl.

4d. This mixture was transformed into strain JM103 and ampicillin resistant clones were selected.

4e. Plasmid was purified from several clones and screened by digestion with MluI or ClaI. Recombinant clones with the new multiple cloning site will give one fragment when digested with either of these enzymes, because each cleaves the plasmid once.

4f. The sequence of the multiple cloning site was verified. This was done by restricting the plasmid with HpaI and PvuII and isolating the 1395 base pair fragment, cloning it into the SmaI site of mp18 and sequencing it by dideoxynucleotide sequencing using standard methods.

4g. This plasmid, called pREV2.2 is diagrammed in FIG. 2 of the drawings.

Example 2—Construction of and expression from pR10

Plasmid pR10, which contains approximately 1275 base pairs of DNA encoding the HTLV-III env gene from essentially the KpnI site to the BglII site, and from which is synthesized an approximately 95 kD fusion protein containing this portion of the gp120 envelope protein, can be constructed as follows:

1. Synthesizing the DNA with the sequence shown in Table 4. This DNA fragment can be synthesized by standard methods (Itakura, et al., supra, and references therein) and encodes a portion of gp120. It has a blunt end on the 4' end and an end which will ligate with a BamHI overhand on the 3' end.
2. Restricting 5 μg of plasmid pBG1 with BclI, filling in the overhanging ends with Klenow polymerase and deoxyribonucleotide triphosphates (dNTPs), restricting this fragment with BamHI and isolating the large fragment, approximately 8.9 kb, from an agarose gel.
3. Ligating 0.1 μg of the fragment in Table 4 with 0.1 μg of the pBG1 fragment in a volume of 20 μl using T4 DNA ligase, transforming the ligation mixture into competent cell strain SG20251 (Gottesman, S., Halpern, E. and Trisler, P. [1981] Journal of Bacteriology 148:265–273), and selecting ampicillin resistant transformants.
4. Selecting, using the AhaIII restriction patter of purified plasmid, cells harboring the recombinant plasmid with the synthesized fragment in the orientation whereby the fragment blunt end ligated to the pBG1 fragment filled-in BclI end and the BamHI overhanging ends ligated together. AhaIII digestion of the proper plasmid gives fragment lengths of approximately 5300, 3170, 690, 640, 330, and 20 base pairs.
5. When the strain harboring this recombinant plasmid is grown in 2% medium (2% yeast extract, bactotryptone, casamino acids (Difco, Detroit, Mich.), 0.2% potassium monobasic, 0.2% potassium dibasic, and 0.2% sodium dibasic) containing 50 μg/ml ampicillin and the total complement of cellular proteins electrophoresed on an SDS-polyacrylamide gel, a prominent protein of approximately 95 kD can be visualized by either coomassie blue staining or by western blot analysis using as probe selected sera from AIDS, ARC, or HTLV-III infected individuals.

Example 3—Purification of recombinant protein containing HTLV-III envelope sequences from plasmid pR10

1. Growth of cells

Cells were grown in a 10 liter volume in a Chemap fermentor (Chemapec, Woodbury, N.Y.) in 2% medium. Fermentation temperature was 37° C., the pH was 6.8, and air was provided at 1 vvm. Plasmid selection was provided by 50 μg/ml ampicillin. Typical cell yield (wet weight) is 30 g/l.

2. Cell lysis 50 g, wet cell weight, of *E. coli* containing the recombinant HTLV-III envelope fusion protein were resuspended in a final volume of 100 ml in 50 mM Tris-Cl pH 8.0, 5 mM ethylenediaminetetraacetic acid (EDTA), 5 mM dithiothreitol (DTT), 15 mM β-mercaptoethanol, 0.5% TRITON ® X-100, and 5 mM phenylmethylsulfonyl fluoride (PMSF). 300 mg lysozyme was added and the suspension incubated for 30 min at room temperature.

This material was lysed using a BEAD-BEATER ™ (Biospec Products, Bartlesville, Okla.) containing an equal volume of 0.1–0.15 μm glass beads. The lysis was done for 6 min at room temperature in 1 min intervals. The liquid was separated from the beads and centrifuged for 2.5 hr at 20,000×g. The supernatant was removed and the pellet dissolved in 100 mL 8M urea, 20 mM Tris-Cl pH 8.0, 5 mM DTT, 15 mM β-mercaptoethanol, 5 mM PMSF, and 1 mM EDTA. The pellet was solubilized using a polytron homogenizer (Beckman, Berkeley, Calif.) and centrifuged at 20,000×g for 2 hr.

3. Diethylaminoethyl (DEAE) chromatography

Supernatant was loaded onto a 550 ml column (5 cm×28 cm) packed with DEAE Fast Flow SE-PHAROSE ® (pharmacia, Piscataway, N.J.) equilibrated in 8M urea, 20 mM Tris-Cl pH 8.0, 15 mM β-mercaptoethanol, and 1 mM KEDTA at room temperature. The column was washed with 1.5 liters equilibration buffer, and the protein eluted with a 5.0 liter linear gradient from 0–0.8% NaCl in equilibration buffer. The HTLV-III protein eluted at 0.2M NaCl and was assayed using SDS-polyacrylamide electrophoresis and following the prominent protein at approximately 95 kD.

The fractions containing the HTLV-III protein were pooled and the protein concentration to 10 ml using a stressed cell positive pressure concentrator (Amicon, Danvers, Mass.) fitted with a 10,000 MW cut-off membrane (YM-10, Amicon). The concentrate was loaded onto a 500 ml column (2.5 cm×100 cm) packed with superfine sephacryl S-300 (Pharmacia) equilibrated in 8M urea, 20 mM Tris-Cl, pH 8.0, 15 mM β-mercaptoethanol, and 1 mM EDTA. The column was eluted with equilibration buffer at room temperature. A flow rate of 0.5 ml/min was maintained. The HTLV-III protein eluted at approximately 40% of the column volume.

Example 4—Construction of and expression from plasmid pPB1IIIB

Plasmid pPB1, which contains approximately 540 base pairs of DNA encoding essentially the HTLV-III env gene from the PvuII site to the BglII site, and from which is synthesized an approximately 26 kD fusion protein containing this portion of the gp120 envelope protein can be constructed as follows:

1. Synthesizing the DNA with the sequence shown in Table 12: This DNA fragment can be synthesized by standard methods and encodes a portion of gp120. It has a blunt end on the 5' end and an end which will ligate with a BamHI overhand on the 3' end.
2. Restricting 5 μg plasmid pREV2.2 with EcoRV and BamHI and isolating the large fragment, approximately 4 kD, from an agarose gel.
3. Ligating 0.1 μg of the fragment in a volume of 20 μl using T4 DNA ligase, transforming the ligation mixture into competent cell strain SG20251, and selecting ampicillin resistant transformants.
4. Using the AhaIII restriction pattern of purified plasmid, selecting cells harboring the recombinant plasmid with the synthesized fragment in the orientation whereby the fragment blunt end ligated to the REV2.2 EcoRV end and the BamHI overhanging ends ligated together. AhaIII digestion of the proper plasmid gives fragment lengths of approximately 1210, 1020, 750, 690, 500, 340, and 20 base pairs. When the strain harboring this recombinant plasmid is grown in 2% medium containing 50 μg/ml ampicillin and the total complement of cellular proteins electrophoresed on an SDS-polyacrylamide gel, a protein of approximately 26 kD can be visualized by either coomassie blue staining or by western blot analysis using as probe selected sera from AIDS, ARC, or HTLV-III infected individuals.

Example 5—Purification of recombinant protein containing HTLV-III envelope sequences from plasmid pPB1IIIB 1. Growth of cells Cells were grown in a 10 liter volume in a Chemap fermentor in 2% medium. Fermentation temperature was 37° C., the pH was 6.8, and air was provided at 1 vvm. Plasmid selection was provided by 50 μg/ml ampicillin and 20 μg/ml chloramphenicol. Typical cell yield (wet weight) was 30 g/l.

2. Cell lysis 50 g, wet cell weight, of *E. coli* containing the recombinant HTLV-III envelope fusion protein were resuspended in a final volume of 100 ml in 50 mM Tris-Cl pH 8.0, 5 mM EDTA, 5 mM DTT, 15 mM β-mercaptoethanol, 0.5% TRITON® X-100, and 5 mM PMSF. 300 mg lysozyme was added and the suspension incubated for 30 min at room temperature.

This material was lysed using a BEAD-BEATER TM (Biospec Products, Bartlesville, Okla.) containing an equal volume of 0.1–0.15 μm glass beads. The lysis was done for 6 min at room temperature in 1 min intervals. The liquid was separated from the beads and centrifuged for 2.5 hr at 20,000×g. The supernatant was removed and the pellet was resuspended in 100 mL 6M guanidine-hydrochloride, 20 mM Tris-Cl pH 8.0, 5 mM DTT, 15 mM β-mercaptoethanol, 5 mM PMSF, and 1 mM EDTA. The pellet was solubilized using a polytron homogenizer and centrifuged at 20,000×g for 2 hr.

The supernate (90 ml) was dialysed against 4 liters of 8M urea, 20 mM potassium phosphate, pH 7.0, 1 mM EDTA, and 15 mM β-mercaptoethanol. Dialysis was done each time for 8 hr or longer with three changes of buffer. Spectraphor dialysis tubing (S/P, McGraw Park, Ill.) with a 3.5 kD MW cut-off was used.

3. CM chromatography

The dialysate was loaded onto a 550 ml column (5 cm×28 cm) packed with CM Fast Flow SEPHAROSE® (Pharmacia) equilibrated in 8M urea, 10 mM potassium phosphate pH 7.0, 15 mM β-mercaptoethanol, and 1 mM EDTA at room temperature. The column was washed with 2 liters equilibration buffer, and the protein eluted with a 5.0 liter linear gradient from 0–0.4M NaCl. The HTLV-III protein (26 kD) eluted at approximately 0.2M NaCl as assayed by SDS-polyacrylamide gel electrophoresis.

Example 6—Construction of and expression from plasmid p590

Plasmid p590, which contains approximately 1055 base pairs of DNA encoding essentially the HTLV-III env gene from the PvuII site to the HindIII site, and from which is synthesized an approximately 86 kD fusion protein containing this portion of the gp160 envelope protein can be constructed as follows:

1. Synthesizing the DNA with the sequence shown in Table 6: This DNA fragment can be synthesized by standard methods and encodes a portion of gp160. It has a blunt end on the 5' end and an end which will ligate with a HindIII overhand on the 3' end.
2. Restricting 5 μg plasmid pREV2.2 with EcoRV and HindIII and isolating the large fragment, approximately 4 kD, from an agarose gel.
3. Ligating 0.1 μg of the fragment in Table 6 with 0.1 μg of the pREV2.2 fragment in a volume of 20 ml using T4 DNA ligase, transforming the ligation mixture into competent cell strain SG20251, and selecting ampicillin resistant transformants.
4. Using the AhaIII restriction pattern of purified plasmid, selecting cells harboring the recombinant plasmid with the synthesized fragment in the orientation whereby the fragment blunt end ligated to the REV2.2 EcoRV end and the HindIII overhanging ends ligated together. AhaIII digestion of the proper plasmid gives fragment lengths of approximately 1740, 1020, 750, 690, 500, 340, and 20.
5. 5 μg of plasmid, purified from this strain, is restricted with NdeI and SmaI. The approximately 1425 base pair fragment is isolated from an agarose gel. The 1505 base pair fragment is fused to the DNA encoding the segment of gp160.
6. 5 μg of pBG101 is restricted with BamHI, the overhanging ends filled in with Klenow polymerase and dNTPs, and then restricted with NdeI. The approximately 6.5 kD fragment is isolated from an agarose gel.
7. Ligating 0.1 μg of the NdeI-SmaI fragment with 0. 1 μg of the pBG1 fragment using T4 DNA ligase, transforming the ligation mixture into competent cell strain SG20251, and selecting ampicillin resistant transformants.
8. Using the AhaIII restriction pattern of purified plasmid, selecting cells harboring the recombinant plasmid with the synthesized fragment in the orientation whereby the fragment blunt SmaI end ligated to the BamHI/filled-in end and the NdeI overhanging ends ligated together. AhaIII digestion of the proper plasmid gives fragment lengths of approximately 5900, 1020, 690, 430, and 20 base pairs.

9. When the strain harboring this recombinant plasmid is grown in 2% medium containing 50 μg/ml ampicillin and the total complement of cellular proteins electrophoresed on an SDS-polyacrylamide gel, a protein of approximately 86 kD can be visualized by either coomassie blue staining or by western blot analysis using as probe selected sera from AIDS, ARC, or HTLV-III infected individuals.

Example 7—Purification of recombinant protein containing HTLV-III envelope sequences from plasmid p590

1. Growth of cells

Cells were grown in a 10 liter volume in a Chemap fermentor in 2% medium. Fermentation temperature was 37° C., the pH was 6.8, and air was provided at 1 vvm. Plasmid selection was provided by 50 μg/ml ampicillin. Typical cell yield (wet weight) was 30 g/l.

2. Cell lysis 50 g, wet cell weight, of *E. coli* containing the recombinant HTLV-III envelope fusion protein were resuspended in a final volume of 100 ml in 50 mM Tris-Cl pH 8.0, 5 mM EDTA, 5 mM DTT, 15 mM β-mercaptoethanol. 0.5% TRITON ® X-100, and 5 mM PMSF. 300 mg lysozyme was added and the suspension incubated for 30 min at room temperature.

This material was lysed using a Bead-Beater ™ containing 0.1–0.15 mm glass beads. The lysis was done for 6 min at room temperature in 1 min intervals. The liquid was separated from the beads and centrifuged for 2.5 hr at 20,000×g. The supernatant was removed and the pellet was resuspended in 100 mL 6M guanidine-hydrochloride, 20 mM Tris-Cl pH 8.0, 5 mM DTT, 15 mM β-mercaptoethanol, 5 mM PMSF, and 1 mM EDTA. The pellet was solubilized using a polytron homogenizer and centrifuged at 20,000×g for 2 hr.

The supernate (90 ml) was dialysed against 4 liters of 8M urea, 20 mM potassium phosphate, pH 8.0, 1 mM EDTA, and 15 mM β-mercaptoethanol. Dialysis was done each time for 8 hr or longer with three changes of buffer.

3. Diethylaminoethyl (DEAE) chromatography

Dialysate was loaded onto a 550 ml column (5 cm×28 cm) packed with DEAE Fast Flow SEPHAROSE ® (Pharmacia) equilibrated in 8M urea, 20 mM Tris-Cl pH 8.0, 15 mM β-mercaptoethanol, and 1 mM EDTA at room temperature. The column was washed with 1.5 liters equilibration buffer, and the protein eluted with a 5.0 liter linear gradient from 0–0.8M NaCl in equilibration buffer. The HTLV-III protein eluted at 0.4M NaCl and was assayed using SDS-polyacrylamide electrophoresis and following the prominent protein at approximately 86 kD.

The fractions containing the HTLV-III protein were pooled and the protein concentrated to 10 ml using a stressed cell positive pressure concentrator (Amicon) fitted with a 10,000 MW cut-off membrane (YM-10, Amicon). The concentrated was loaded onto a 500 ml column (2.5 cm×100 cm) packed with superfine SEPHACRYL ®S-300 (Pharmacia) equilibrated in 8M urea, 20 mM Tris-Cl, pH 8.0, 15 mM β-mercaptoethanol, and 1 mM EDTA. The column was eluted with equilibration buffer at room temperature. A flow rate of 0.5 ml/min was maintained. The HTLV-III protein eluted at approximately 40% of the column volume.

Example 18—Construction of and expression from plasmid pKH1

Plasmid pKH1, which contains approximately 1830 base pairs of DNA encoding essentially the HTLV-III env gene from the KpnI site to the HindIII site, and from which is synthesized an approximately 70 kD fusion protein containing this portion of the gp160 envelope protein, can be constructed as follows:

1. Synthesizing the DNA with the sequence shown in Table 7: This DNA fragment can be synthesized by standard methods and encodes a portion of gp160. It has a blunt end on the 5' end and an end which will ligate with a HindIII overhand on the 3' end.
2. Restricting 5 μg plasmid pREV2.2 with MluI, treating the DNA with Klenow polymeraise to blunt the ends, treating with HindIII and isolating the large fragment, approximately 5 kD, from an agarose gel.
3. Ligating 0.1 μg of the fragment in Table 7 with 0.1 μg of the pREV 2.2 fragment in a volume of 20 μl using T4 DNA ligase, transforming the ligation mixture into competent cell strain CAG629, and selecting ampicillin resistant transformants.
4. Using the AhaIII restriction pattern of purified plasmid, selecting cells harboring the recombinant plasmid with the synthesized fragment in the orientation whereby the fragment blunt end ligated to the REV2.2 MluI end and the HindIII overhanging ends ligated together. AhaIII digestion of the proper plasmid gives fragment lengths of approximately 1730, 1020, 750, 690, 640, 600, 340, and 20 base pairs. When the strain harboring this recombinant plasmid is grown in 2% medium containing 50 μg/ml ampicillin and the total complement of cellular proteins electrophoresed on an SDS-polyacrylamide gel, a protein of approximately 70 kD can be visualized by either Coomassie blue staining or by Western Blot analysis using as probe selected sera from AIDS, ARC, or HTLV-III infected individuals.

Example 9—Purification of recombinant protein containing HTLV-III envelope sequences from plasmid pKH1

1. Growth of cells

Cells were grown in a 10 liter volume in a Chemap fermentor in 2% medium. Fermentation temperature was 32° C., the pH was 6.8, and air was provided at 1 vvm. Plasmid selection was provided by 50 μg/ml ampicillin. Typical cell yield (wet weight) is 30 g/l.

2. Cell lysis 50 g, wet cell weight, of *E. coli* containing the recombinant HTLV-III envelope fusion protein were resuspended in a final volume of 100 ml in 50 mM Tris-Cl pH 8.0, 5 mM EDTA, 5 mM dithiothreitol (DTT), 15 mM β-mercaptoethanol, 0.5% TRITON ® X-100 and 5 mM PMSF. 300 mg lysozyme was added and the suspension incubated for 30 min at room temperature.

This material was lysed using a BEADBEATER ™ (Biospec Products) containing an equal volume of 0.1–0.15 μm glass beads. The lysis was done for 6 min at room temperature in 1 min intervals. The liquid was separated from the beads and centrifuged for 2.5 hr at 20,000×g. The supernatant was removed and the pellet dissolved in 100 ml 8M urea, 20 mM Tris-Cl pH 8.0, 5 mM DTT, 15 mM β-mercaptoethanol, 5 mM PMSF, and 1 mM EDTA. The pellet was solubilized using a polytron homogenizer (Beckman, Berkeley, Calif.) and centrifuged at 20,000×g for 2 hr.

3. DEAE chromatography

Supernatant was loaded onto a 550 ml column (5 cm×28 cm) packed with DEAE Fast Flow SEPHAROSE® (Pharmacia) equilibrated in 8M urea, 20 mM Tris-Cl pH 8.0, 15 mM β-mercaptoethanol, and 1 mM EDTA at room temperature. The column was washed with 1.5 liters equilibration buffer, and the protein eluted with a 5.0 liter linear gradient from 0–0.8M NaCl in equilibration buffer. The HTLV-III protein eluted at 0.2M NaCl and was assayed using SDS-polyacrylamide electrophoresis and following the protein at approximately 70 kD.

The fractions containing the HTLV-III protein were pooled and the protein concentrated to 10 ml using a stressed cell positive pressure concentrator (Amicon) fitted with a 10,000 MW cut-off membrane (YM-10, Amicon). The concentrate was loaded onto a 500 ml column (2.5 cm×100 cm) packed with superfine SEPHACRYL®S-300 (Pharmacia) equilibrated in 8M urea, 20 mM Tris-Cl, pH 8.0, 15 mM β-mercaptoethanol, and 1 mM EDTA. The column was eluted with equilibration buffer at room temperature. A flow rate of 0.5 ml/min was maintained. The HTLV-III protein eluted at approximately 40% of the column volume.

4. SDS-polyacrylamide electrophoresis:

The fractions containing KH1 were pooled and the protein concentrated using a stressed cell positive pressure concentrator fitted with a 10,000 MW cutoff membrane. 2 mg of protein was mixed with loading buffers and electrophoresed through a preparative SDS-polyacrylamide gel (40 cm×20 cm×4 mm) as described by M. W. Hunkapiller, E. Lujan, F. Ostrander, and L. E. Hood, Methods in Enzymology 91:227–236 (1983). The 70 kD HTLV-III protein was visualized with 0.25M KCl and eluted from the gel as described. The protein can be removed from the SDS by precipitation with acetone (Dynan, W. J. Jendrisak, J. J., Hager, D. A. and Burgess, R. R. [1981] J. Biol. Chem. 256:5860–5865).

Example 10—Construction of a non-fusion derivative of PB1

A non-fusion derivative of the PB1 protein containing no non-HTLV-III amino acids other than an N-terminal methionine was constructed using oligonucleotide-directed site-specific mutagensis (Inouye, S. and Inouye, M., "Synthesis & Applications of DNA & RNA", ed. Narang, Saran A. Academic Press, 1987). In this procedure, 90 non-HTLV-III bp upstream and 39 downstream of the env gene sequence in pPB1 were deleted via DNA loopouts generated by hybridization with synthetic oligonucleotides.

The oligonucleotide synthesized for the N-terminal loopout was designed so that the start codon of the β-glucuronidase gene is placed immediately adjacent to the 5' end of the HTLV-III env gene sequence (FIG. 4). The oligonucleotide includes sequences homologous to both sides of this newly-created junction that allow proper hybridization to the plasmid DNA.

The two DNA molecules used to form a heteroduplex with a single-stranded gap that is the substrate for hybridization were created by digesting pPB1 with SalI and HpaI, or with PstI alone. Digestion with PstI linearized pPB1, and a double digest with SalI and HpaI yields fragments of 3800 and 700 bp, the larger of which was gel-isolated for use in the mutagenesis.

Kinasing of the oligonucleotide, hybridization, polymerization and ligation to yield closed circular molecules were done according to the methods of Inouye and Inouye mentioned above. To enrich for DNA molecules containing the deletion, the DNA mixture was digested with MluI, which cuts within the region being deleted.

The digested DNA was used to transform competent *E. coli* JM105 cells and plasmid-containing transformants were isolated by overnight growth on YT (8 g tryptone, 5 g yeast extract, and 5 g NaCl per liter) Cm plates at 37° C.

Plasmid DNA was isolated from each transformant and screened for the correct construction by simultaneous digestion with MluI and HindIII. Molecules that were not deleted yielded fragments of approximately 3900 and 600 bp. Those containing the deletion did not have the MluI site and yielded linear molecules of approximately 4400 bp. Plasmid DNA from transformants that appeared to contain the deletion was retransformed to ensure segregation of deleted and non-deleted plasmids and the recovery of pure plasmid populations. DNA from these second transformants was analyzed as in the previous digest and was determined to have the correct construction. This plasmid was designated pΔPB1.

To eliminate the C-terminal non-HTLV-III amino acids, oligonucleotide-directed site-specific mutagenesis was carried out as above, using the pΔPB1 plasmid as a substrate. The oligonucleotide (FIG. 5) was designed to position the TGA codon that occurs out-of-frame downstream from the env gene sequence so that it is immediately adjacent to the 3′ end of the env gene sequence and in-frame to act as a translational stop codon.

The molecules to form the heteroduplex used for hybridization were created by digesting pΔPB1 with PstI alone or with KpnI and HpaI. The large KpnI/HpaI fragment encompassing most of the vector was gel-isolated for use in the mutagenesis. Kinasing, hybridization, polymerization and ligation were performed as above. Enrichment for deleted molecules was accomplished by digesting with HindIII, which cuts within the region being deleted. The DNA was used to transform cells as above.

Plasmid DNA was isolated from each transformant and screened for the correct construction by simultaneous digestion with EcoRI and HpaI. The deleted plasmid yields two restriction fragments of 2900 and 1750 bp. Plasmid DNA showing this pattern was retransformed as above, and DNA from these transformants was analyzed with the same digest. This plasmid, containing N-terminal and C-terminal deletions, is designated pd2PB1.

When the strain harboring plasmid pΔPB1 is grown in 2% medium (2% yeast extract, bactotryptone, casamino acids [Difco, Detroit, Mich.], 0.2% potassium monobasic, 0.2% potassium dibasic, and 0.2% sodium dibasic) containing 50 μg/ml ampicillin and the total complement of cellular proteins electrophoresed on an SDS-polyacrylamide gel, a protein of approximately 22 kD can be visualized by either coomassie blue staining or by western blot analysis using as probe selected sera from animals immunized with recombinant env gene proteins. Under the same conditions, a protein of approximately 20 kD is produced in a strain containing pd2PB1.

The technique of oligonucleotide-directed site-specific mutagenesis can be used in a similar way to eliminate the non-HTLV-III amino acids flanking the env gene fusion proteins R10, 590, and KH1.

In the procedure detailed above, the removal of the non-HTLV-III sequences from the fusion proteins involves removal of amino acids at both the N-terminus and the C-terminus of the protein and is accomplished in two sequential steps.

It is well known in the art that a methionine at the N-terminal position can be enzymatically cleaved by the use of the enzyme methionine aminopeptidase (MAP). MAP has been cloned from *E. coli* (Ben-Bassat, A., Bauer, K., Chang, S.-Y., Myanbo, K., Boosman, A. and Chang, S. [1987] Journal of Bacteriology 169(2):751-757) and *Salmonella typhimurium*, and in vitro activity has been demonstrated on recombinant proteins (Miller, C. G., Stracuch, K. L., Kukral, A. M., Miller, J. L., Wingfield, P. T., Massei, G. J., Werlen, R. C., Graber, P. and Movva, N. R. [1987] Proc. Natl. Acad. Sci. USA 84:2718-2722). Therefore, removal of an N-terminal methionine may be achieved either in vivo by expressing the protein in a host which produces MAP (e.g., *E. coli* CM89 or *S. cerevisiae*), or in vitro by use of purified MAP (e.g., procedure of Miller et al.).

pd2PB1 Purification

Unless specified otherwise, all steps are carried out at room temperature.

Lysis—Three 700 ml bottles of frozen cell paste containing pd2PB1 are thawed at 37° C., and are then spun at 4,000 rpm in a J-6B centrifuge with a JS-4.2 rotor (Beckman, Palo Alto, Calif.) at 4° C. for 30 min. The supernatant is then discarded and the weight of the cell pellet is determined. The cell pellet (typically 1 kg) is resuspended in 2 volumes of lysis buffer (v/w) which consists of 8M urea, 20 mM Tris-HCl (pH 7.5±0.1), 1 mM EDTA, 14.7 nM 2-mercaptoethanol and 1 mM PMSF.

The resuspended cell pellet is run through a Type TDK Pilot DYNO-MILL® (Impandex Inc., Maywood, N.J.) containing 0.5–0.7 mm glass beads at 200–400 ml/min. Prior to use the DYNO-MILL® is charged with one liter of lysis buffer and cooled so that the solution flowing through is at less than ambient temperature. The resuspended cell pellet is passed through the DYNO-MILL® twice, and after the second pass, the DYNO-MILL® is washed with 1 liter of lysis buffer. Lysed cell suspension and wash are pooled.

Concentration and filtration—The lysed cell suspension plus one liter wash is concentrated to 800 ml using a 0.45 micron DURAPORE™ Pellicon cassette in a Pellicon 4 GPM system (Millipore, Bedford, Mass.). The concentration is done with an inlet pressure of less than or equal to 40 psi and an outlet pressure between 10 and 20 psi. After concentration the lysed cell suspension is filtered with 4 liters of lysis buffer using the same Pellicon system, cassette and pressure settings with the tubing rigged for dyafiltration.

Extraction—The washed lysis cell suspension is extracted with 10 l of extraction buffer consisting of 6M guanidine HCl, 100 mM Tris-HCl (pH 7.6±0.1), and 10 mM EDTA, using the same Pellicon system, cassette and pressure settings as described above with the tubing rigged for dyafiltration.

Buffer exchange—The filtrate from the previous step is typically concentrated to 1 liter using a Pellicon 4GPM system with two PTGC cassettes (10,000 NMWL). The concentration is done with an inlet pressure of less than or equal to 50 psi and an outlet pressure between 30 and 45 psi. After concentration, the supernatant is buffer exchanged with CM column buffer consisting of 8M urea, 25 mM potassium phosphate, and 1 mM EDTA (pH 6.8±0.1), with conductivity less than or equal to 3.0 ms/cm. For buffer exchange, the same Pellicon system, the same cassettes and the same pressure settings as above are used with the tubing rigged for dyafiltration. Eight liters of CM column buffer are used to buffer exchange 1 liter of concentrated extract. After buffer exchange, the buffer-exchanged extract is drained from the system and the system is washed with 1 liter of CM column buffer. The buffer-exchanged extract and the wash are pooled and the solution's conductivity and pH are measured. The conductivity of the solution is adjusted to less than or equal to 3.0 ms/cm with deionized 8M urea and the pH is adjusted to be within the range of 6.5–7.0.

CM chromatography—A 50×51 cm column of CM SEPHAROSE® FAST FLOW (Pharmacia, Piscataway, N.J.) is equilibrated by washing the column sequentially with 4 column volumes of 0.5M NaOH, 2 column volumes of deionized water and 2–3 column volumes of CM column buffer. The column is considered equilibrated when the pH of the outflow is within 0.2 units of the CM column buffer and the conductivity of the outflow is within 0.3 ms/cm of the CM column buffer.

For loading, the buffer exchanged extract is pumped on to the column at an inlet pressure between 10 and 15 psi. After loading, the CM column is washed with CM column buffer until the OD at 280 nm of the outflow is less than 0.1. The pd2PB1 is then eluted with an 8-liter linear gradient of 0–0.5M NaCl in CM column buffer and collected in 100 ml fractions. The fractions are assayed by SDS-PAGE and Western with anti-gp160 antibody, and those containing significant pd2PB1 and trace contaminants are pooled.

Organic extraction—The pooled protein solution from the previous step is brought to a ratio of 55% acetonitrile to 45% protein solution (v/v) by the slow addition of pure acetonitrile with mixing. After addition of all of the acetonitrile, the solution is centrifuged in a J2-21 centrifuge using a JA10 rotor (Beckman) at 10,000 rpm and 4° C. for 15 min. After centrifugation, the supernatant is collected and the pellet is discarded.

The centrifugation supernatant is brought to a ratio of 35% ethanol to 65% supernatant (v/v) by slow addition of 95% ethanol with mixing. After addition of al of the ethanol, the solution is centrifuged in a J2-21 centrifuge using a JA-10- rotor at 10,000 rpm and 4° C. for 15 min. After centrifugation the pellet is collected and the supernatant is discarded.

The pellet is allowed to air dry for 15 min, and is then redissolved in S-300 column buffer, which consists of 8M urea, 0.3M glycine, 5 mM EDTA, 15 mM 2-mercaptoethanol, 1mM dithiothreitol (DTT) (pH 8.50±0.01). The pellet is dissolved in a volume of S-300 column buffer equal to one-tenth the volume of the pooled protein solution at the beginning of this step.

Concentration—The absorbance of the redissolved protein solution from above is determined at 280 nm and an approximate protein concentration is determined by assuming of 1.0 at 280 nm. The solution is concentrated to 10 mg/ml using a 200 ml Amicon stirred cell concentrator with a YM-10 membrane.

S-300 chromatography—Thirty to seventy ml of the concentrated protein solution is loaded on a 5.0×135 cm column of SEPHACRYL ® S-300 from Pharmacia. The column had been previously equilibrated with S-300 column buffer which consists of 8M urea, 0.3M glycine, 5 mM EDTA, 15 mM 2-mercaptoethanol, 1 mM DTT (pH 8.50±0.01). After loading, the column is run isocratically in the same buffer. Twenty ml fractions are collected and the fractions are assayed for pd2PB1 content by SDS-PAGE.

Equal volume aliquots are taken from suitable fractions containing pd2PB1 and are used to determine which fractions are satisfactory for pooling. The aliquots are pooled, dialyzed overnight versus 8M urea, 25 mM sodium phosphate, 1 mM EDTA (pH 6.8±0.1), and the OD at 280 nm of the dialyzed pool is determined using the dialysis buffer as blank. The protein concentration of the solution is determined using the calculated extinction coefficient of pd2PB1 of 1.0 $(mg/ml)^{-1}$. SDS-PAGE is run on 10 μg of the dialyzed pooling using a 15% SDS acrylamide gel. After coomassie staining and destaining, the gel is scanned using an LKB (Gaithersburg, Md.) scanning densitometer attached to a Waters (Milford, Mass.) 740 Integrator. If the pd2PB1 band on the gel is more than 97% pure, then the fractions that were used for the aliquot are checked for endotoxins at a 1 to 20 dilution in the Limulus Amebocyte Lysate (LAL) assay using 0.06 eu/ml tubes. If the LAL test on the diluted fractions is negative, the fractions are pooled and used for subsequent operations. If the gel fails to meet the purity specification, the process is repeated using equal volume aliquots from a different set of fractions. Only those fractions having a negative LAL test at a 1 to 20 dilution are pooled.

TABLE 1

```
5' GATCAAGCTTCTGCAGTCGACGCATGCGGATCCGGTACCCGGGAGCTCG 3'
   TTCGAAGACGTCAGCTGCGTACGCCTAGGCCATGGGCCCTCGAGCTTAA
```

TABLE 2

```
5'    CGGTACCAGCCCGCCTAATGAGCGGGCTTTTTTTTGACGT 3'
      TGCAGCCATGGTCGGGCGGATTACTCGCCCGAAAAAAAAC
```

TABLE 3

| MluI | EcoRV | ClaI | BamHI | SalI | HindIII | SmaI |
|------|-------|------|-------|------|---------|------|

```
CGAACGCGTGGCCGATATCATCGATGGATCCGTCGACAAGCTTCCCGGGAGCT
GCTTGCGCACCGGCTATAGTAGCTACCTAGGCAGCTGTTCGAAGGGCCC
```

TABLE 4

```
                              5'    AATTCCCTGTGTGGAAGGAAGCA
                                    TTAAGGGACACACCTTCCTTCGT

ACCACCACTCTATTTTGTGCATCAGATGCTAAAGCATATGATACAGAGGTACAT
TGGTGGTGAGATAAAACACGTAGTCTACGATTTCGTATACTATGTCTCCATGTA

AATGTTTGGGCCACACATGCCTGTGTACCCACAGACCCCAACCCACAAGAAGTA
TTACAAACCCGGTGTGTACGGACACATGGGTGTCTGGGGTTGGGTGTTCTTCAT

GTATTGGTAAATGTGACAGAAAATTTTAACATGTGGAAAAATGACATGGTAGAA
CATAACCATTTACACTGTCTTTTAAAATTGTACACCTTTTACTGTACCATCTT

CAGATGCATGAGGATATAATCAGTTTATGGGATCAAAGCCTAAAGCCATGTGTA
GTCTACGTACTCCTATATTAGTCAAATACCCTAGTTTCGGATTTCGGTACACAT

AAATTAACCCCACTCTGTGTTAGTTTAAAGTGCACTGATTTGAAGAATGATACT
TTTAATTGGGGTGAGACACAATCAAATTTCACGTGACTAAACTTCTTACTATGA

AATACCAATAGTAGTAGCGGGAGAATGATAATGGAGAAAGGAGAGATAAAAAAC
TTATGGTTATCATCATCGCCCTCTTACTATTACCTCTTTCCTCTCTATTTTTG

TGCTCTTTCAATATCAGCACAAGCATAAGAGGTAAGGTGCAGAAAGAATATGCA
ACGAGAAAGTTATAGTCGTGTTCGTATTCTCCATTCCACGTCTTTCTTATACGT

TTTTTTTATAAACTTGATATAATACCAATAGATAATGATACTACCAGCTATACG
AAAAAAATATTTGAACTATATTATGGTTATCTATTACTATGATGGTCGATATGC

TTGACAAGTTGTAACACCTCAGTCATTACACAGGCCTGTCCAAAGGTATCCTTT
AACTGTTCAACATTGTGGAGTCAGTAATGTGTCCGGACAGGTTTCCATAGGAAA

GAGCCAATTCCCATACATTATTGTGCCCCGGCTGGTTTTGCGATTCTAAAATGT
CTCGGTTAAGGGTATGTAATAACACGGGGCCGACCAAAACGCTAAGATTTTACA

AATAATAAGACGTTCAATGGAACAGGACCATGTACAAATGTCAGCACAGTACAA
TTATTATTCTGCAAGTTACCTTGTCCTGGTACATGTTTACAGTCGTGTCATGTT

TGTACACATGGAATTAGGCCAGTAGTATCAACTCAACTGCTGTTAAATGGCAGT
ACATGTGTACCTTAATCCGGTCATCATAGTTGAGTTGACGACAATTTACCGTCA

CTAGCAGAAGAAGAGGTAGTAATTAGATCTGCCAATTTCACAGACAATGCTAAA
GATCGTCTTCTTCTCCATCATTAATCTAGACGGTTAAAGTGTCTGTTACGATTT
```

TABLE 4-continued

```
ACCATAATAGTACAGCTGAACCAATCTGTAGAAATTAATTGTACAAGACCCAAC
TGGTATTATCATGTCGACTTGGTTAGACATCTTTAATTAACATGTTCTGGGTTG

AACAATACAAGAAAAAGTATCCGTATCCAGAGAGGACCAGGGAGAGCATTTGTT
TTGTTATGTTCTTTTTCATAGGCATAGGTCTCTCCTAATCCCTCTCGTAAACAA

ACAATAGGAAAAATAGGAAATATGAGACAAGCACATTGTAACATTAGTAGAGCA
TGTTATCCTTTTTATCCTTTATACTCTGTTCGTGTAACATTGTAATCATCTCGT

AAATGGAATAACACTTTAAAACAGATAGATAGCAAATTAAGAGAACAATTTGGA
TTTACCTTATTGTGAAATTTTGTCTATCTATCGTTTAATTCTCTTGTTAAACCT

AATAATAAAACAATAATCTTTAAGCAGTCCTCAGGAGGGGACCCAGAAATTGTA
TTATTATTTTGTTATTAGAAATTCGTCAGGAGTCCTCCCCTGGGTCTTTAACAT

ACGCACAGTTTTAATTGTGGAGGGGAATTTTTCTACTGTAATTCAACACAACTG
TGCGTGTCAAAATTAACACCTCCCCTTAAAAAGATGACATTAAGTTGTGTTGAC

TTTAATAGTACTTGGTTTAATAGTACTTGGAGTACTAAAGGGTCAAATAACACT
AAATTATCATGAACCAAATTATCATGAACCTCATGATTTCCCAGTTTATTGTGA

GAAGGAAGTGACACAATCACCCTCCCATGCAGAATAAAACAAATTATAAACATG
CTTCCTTCACTGTGTTAGTGGGAGGGTACGTCTTATTTTGTTTAATATTTGTAC

TGGCAGGAAGTAGGAAAAGCAATGTATGCCCCTCCCATCAGTGGACAAATTAGA
ACCGTCCTTCATCCTTTTCGTTACATACGGGGAGGGTAGTCACCTGTTTAATCT

TGTTCATCAAATATTACAGGGCTGCTATTAACAAGAGATGGTGGTAATAGCAAC
ACAAGTAGTTTATAATGTCCCGACGATAATTGTTCTCTACCACCATTATCGTTG

AATGAGTCCGA          3'
TTACTCAGGCTCTAG
```

TABLE 5

```
5'   CTGAACCAATCTGTAGAAATTAATTGTACAAGACCCAAC
     GACTTGGTTAGACATCTTTAATTAACATGTTCTGGGTTG

AACAATACAAGAAAAAGTATCCGTATCCAGAGAGGACCAGGGAGAGCATTTGTT
TTGTTATGTTCTTTTTCATAGGCATAGGTCTCTCCTGGTCCCTCTCGTAAACAA

ACAATAGGAAAAATAGGAAATATGAGACAAGCACATTGTAACATTAGTAGAGCA
TGTTATCCTTTTTATCCTTTATACTCTGTTCGTGTAACATTGTAATCATCTCGT

AAATGGAATAACACTTTAAAACAGATAGATAGCAAATTAAGAGAACAATTTGGA
TTTACCTTATTGTGAAATTTTGTCTATCTATCGTTTAATTCTCTTGTTAAACCT

AATAATAAAACAATAATCTTTAAGCAGTCCTCAGGAGGGGACCCAGAAATTGTA
TTATTATTTTGTTATTAGAAATTCGTCAGGAGTCCTCCCCTGGGTCTTTAACAT

ACGCACAGTTTTAATTGTGGAGGGGAATTTTTCTACTGTAATTCAACACAACTG
TGCGTGTCAAAATTAACACCTCCCCTTAAAAAGATGACATTAAGTTGTGTTGAC

TTTAATAGTACTTGGTTTAATAGTACTTGGAGTACTAAAGGGTCAAATAACACT
AAATTATCATGAACCAAATTATCATGAACCTCATGATTTCCCAGTTTATTGTGA

GAAGGAAGTGACACAATCACCCTCCCATGCAGAATAAAACAAATTATAAACATG
CTTCCTTCACTGTGTTAGTGGGAGGGTACGTCTTATTTTGTTTAATATTTGTAC

TGGCAGGAAGTAGGAAAAGCAATGTATGCCCCTCCCATCAGTGGACAAATTAGA
ACCGTCCTTCATCCTTTTCGTTACATACGGGGAGGGTAGTCACCTGTTTAATCT

TGTTCATCAAATATTACAGGGCTGCTATTAACAAGAGATGGTGGTAATAGCAAC
ACAAGTAGTTTATAATGTCCCGACGATAATTGTTCTCTACCACCATTATCGTTG

AATGAGTCCGA          3'
TTACTCAGGCTCTAG
```

TABLE 6

```
5'    CTGAACCAATCTGTAGAAATTAATTGTACAAGACCCAAC
      GACTTGGTTAGACATCTTTAATTAACATGTTCTGGGTTG

AACAATACAAGAAAAAGTATCCGTATCCAGAGAGGACCAGGGAGAGCATTTGTT
TTGTTATGTTCTTTTTCATAGGCATAGGTCTCTCCTGGTCCCTCTCGTAAACAA

ACAATAGGAAAAATAGGAAATATGAGACAAGCACATTGTAACATTAGTAGAGCA
TGTTATCCTTTTTATCCTTTATACTCTGTTCGTGTAACATTGTAATCATCTCGT

AAATGGAATAACACTTTAAAACAGATAGATAGCAAATTAAGAGAACAATTTGGA
```

TABLE 6-continued

```
TTTACCTTATTGTGAAATTTTGTCTATCTATCGTTTAATTCTCTTGTTAAACCT

AATAATAAAACAATAATCTTTAAGCAGTCCTCAGGAGGGGACCCAGAAATTGTA
TTATTATTTTGTTATTAGAAATTCGTCAGGAGTCCTCCCCTGGGTCTTTAACAT

ACGCACAGTTTTAATTGTGGAGGGGAATTTTTCTACTGTAATTCAACACAACTG
TGCGTGTCAAAATTAACACCTCCCCTTAAAAAGATGACATTAAGTTGTGTTGAC

TTTAATAGTACTTGGTTTAATAGTACTTGGAGTACTAAAGGGTCAAATAACACT
AAATTATCATGAACCAAATTATCATGAACCTCATGATTTCCCAGTTTATTGTGA

GAAGGAAGTGACACAATCACCCTCCCATGCAGAATAAAACAAATTATAAACATG
CTTCCTTCACTGTGTTAGTGGGAGGGTACGTCTTATTTTGTTTAATATTTGTAC

TGGCAGGAAGTAGGAAAAGCAATGTATGCCCCTCCCATCAGTGGACAAATTAGA
ACCGTCCTTCATCCTTTTCGTTACATACGGGGAGGGTAGTCACCTGTTTAATCT

TGTTCATCAAATATTACAGGGCTGCTATTAACAAGAGATGGTGGTAATAGCAAC
ACAAGTAGTTTATAATGTCCCGACGATAATTGTTCTCTACCACCATTATCGTTG

AATGAGTCCGAGATCTTCAGACCTGGAGGAGGAGATATGAGGGACAATTGGAGA
TTACTCAGGCTCTAGAAGTCTGGACCTCCTCCTCTATACTCCCTGTTAACCTCT

AGTGAATTATATAAATATAAAGTAGTAAAAATTGAACCATTAGGAGTAGCACCC
TCACTTAATATATTTATATTTCATCATTTTTAACTTGGTAATCCTCATCGTGGG

ACCAAGGCAAAGAGAAGAGTGGTGCAGAGAGAAAAAAGAGCAGTGGGAATAGGA
TGGTTCCGTTTCTCTTCTCACCACGTCTCTCTTTTTTCTCGTCACCCTTATCCT

GCTTTGTTCCTTGGGTTCTTGGGAGCAGCAGGAAGCACTATGGGCGCAGCGTCA
CGAAACAAGGAACCCAAGAACCCTCGTCGTCCTTCGTGATACCCGCGTCGCAGT

ATGACGCTGACGGTACAGGCCAGACAATTATTGTCTGGTATAGTGCAGCAGCAG
TACTGCGACTGCCATGTCCGGTCTGTTAATAACAGACCATATCACGTCGTCGTC

AACAATTTGCTGAGGGCTATTGAGGCGCAACAGCATCTGTTGCAACTCACAGTC
TTGTTAAACGACTCCCGATAACTCCGCGTTGTCGTAGACAACGTTGAGTGTCAG

TGGGGCATCAAGCAGCTCCAGGCAAGAATCCTGGCTGTGGAAAGATACCTAAAG
ACCCCGTAGTTCGTCGAGGTCCGTTCTTAGGACCGACACCTTTCTATGGATTTC

GATCAACAGCTCCTGGGGATTTGGGGTTGCTCTGGAAAACTCATTTGCACCACT
CTAGTTGTCGAGGACCCCTAAACCCCAACGAGACCTTTTGAGTAAACGTGGTGA

GCTGTGCCTTGGAATGCTAGTTGGAGTAATAAATCTCTGGAACAGATTTGGAAT
CGACACGGAACCTTACGATCAACCTCATTATTTAGAGACCTTGTCTAAACCTTA

AACATGACCTGGATGGAGTGGGACAGAGAAATTAACAATTACACA         3'
TTGTACTGGACCTACCTCACCCTGTCTCTTTAATTGTTAATGTGTTCGA
```

TABLE 7

```
                   5'      AATTCCCTGTGTGGAAGGAAGCA
                           TTAAGGGACACACCTTCCTTCGT

ACCACCACTCTATTTTGTGCATCAGATGCTAAAGCATATGATACAGAGGTACAT
TGGTGGTGAGATAAAACACGTAGTCTACGATTTCGTATACTATGTCTCCATGTA

AATGTTTGGGCCACACATGCCTGTGTACCCACAGACCCCAACCCACAAGAAGTA
TTACAAACCCGGTGTGTACGGACACATGGGTGTCTGGGGTTGGGTGTTCTTCAT

GTATTGGTAAATGTGACAGAAAATTTTAACATGTGGAAAAATGACATGGTAGAA
CATAACCATTTACACTGTCTTTTAAAATTGTACACCTTTTACTGTACCATCTT

CAGATGCATGAGGATATAATCAGTTTATGGGATCAAAGCCTAAAGCCATGTGTA
GTCTACGTACTCCTATATTAGTCAAATACCCTAGTTTCGGATTTCGGTACACAT

AAATTAACCCCACTCTGTGTTAGTTTAAAGTGCACTGATTTGAAGAATGATACT
TTTAATTGGGGTGAGACACAATCAAATTTCACGTGACTAAACTTCTTACTATGA

AATACCAATAGTAGTAGCGGGAGAATGATAATGGAGAAAGGAGAGATAAAAAAC
TTATGGTTATCATCATCGCCCTCTTACTATTACCTCTTTCCTCTCTATTTTTTG

TGCTCTTTCAATATCAGCACAAGCATAAGAGGTAAGGTGCAGAAAGAATATGCA
ACGAGAAAGTTATAGTCGTGTTCGTATTCTCCATTCCACGTCTTTCTTATACGT

TTTTTTTATAAACTTGATATAATACCAATAGATAATGATACTACCAGCTATACG
AAAAAAATATTTGAACTATATTATGGTTATCTATTACTATGATGGTCGATATGC

TTGACAAGTTGTAACACCTCAGTCATTACACAGGCCTGTCCAAAGGTATCCTTT
AACTGTTCAACATTGTGGAGTCAGTAATGTGTCCGGACAGGTTTCCATAGGAAA
```

TABLE 7-continued

```
GAGCCAATTCCCATACATTATTGTGCCCCGGCTGGTTTTGCGATTCTAAAATGT
CTCGGTTAAGGGTATGTAATAACACGGGGCCGACCAAAACGCTAAGATTTTACA

AATAATAAGACGTTCAATGGAACAGGACCATGTACAAATGTCAGCACAGTACAA
TTATTATTCTGCAAGTTACCTTGTCCTGGTACATGTTTACAGTCGTGTCATGTT

TGTACACATGGAATTAGGCCAGTAGTATCAACTCAACTGCTGTTAAATGGCAGT
ACATGTGTACCTTAATCCGGTCATCATAGTTGAGTTGACGACAATTTACCGTCA

CTAGCAGAAGAAGAGGTAGTAATTAGATCTGCCAATTTCACAGACAATGCTAAA
GATCGTCTTCTTCTCCATCATTAATCTAGACGGTTAAAGTGTCTGTTACGATTT

ACCATAATAGTACAGCTGAACCAATCTGTAGAAATTAATTGTACAAGACCCAAC
TGGTATTATCATGTCGACTTGGTTAGACATCTTTAATTAACATGTTCTGGGTTG

AACAATACAAGAAAAAGTATCCGTATCCAGAGAGGACCAGGGAGAGCATTTGTT
TTGTTATGTTCTTTTTCATAGGCATAGGTCTCTCCTAATCCCTCTCGTAAACAA

ACAATAGGAAAAATAGGAAATATGAGACAAGCACATTGTAACATTAGTAGAGCA
TGTTATCCTTTTTATCCTTTATACTCTGTTCGTGTAACATTGTAATCATCTCGT

AAATGGAATAACACTTTAAAACAGATAGATAGCAAATTAAGAGAACAATTTGGA
TTTACCTTATTGTGAAATTTTGTCTATCTATCGTTTAATTCTCTTGTTAAACCT

AATAATAAAACAATAATCTTTAAGCAGTCCTCAGGAGGGGACCCAGAAATTGTA
TTATTATTTTGTTATTAGAAATTCGTCAGGAGTCCTCCCCTGGGTCTTTAACAT

ACGCACAGTTTTAATTGTGGAGGGGAATTTTTCTACTGTAATTCAACACAACTG
TGCGTGTCAAAATTAACACCTCCCCTTAAAAAGATGACATTAAGTTGTGTTGAC

TTTAATAGTACTTGGTTTAATAGTACTTGGAGTACTAAAGGGTCAAATAACACT
AAATTATCATGAACCAAATTATCATGAACCTCATGATTTCCCAGTTTATTGTGA

GAAGGAAGTGACACAATCACCCTCCCATGCAGAATAAAACAAATTATAAACATG
CTTCCTTCACTGTGTTAGTGGGAGGGTACGTCTTATTTTGTTTAATATTTGTAC

TGGCAGGAAGTAGGAAAAGCAATGTATGCCCCTCCCATCAGTGGACAAATTAGA
ACCGTCCTTCATCCTTTTCGTTACATACGGGGAGGGTAGTCACCTGTTTAATCT

TGTTCATCAAATATTACAGGGCTGCTATTAACAAGAGATGGTGGTAATAGCAAC
ACAAGTAGTTTATAATGTCCCGACGATAATTGTTCTCTACCACCATTATCGTTG

AATGAGTCCGAGATCTTCAGACCTGGAGGAGGAGATATGAGGGACAATTGGAGA
TTACTCAGGCTCTAGAAGTCTGGACCTCCTCCTCTATACTCCCTGTTAACCTCT

AGTGAATTATATAAATATAAAGTAGTAAAAATTGAACCATTAGGAGTAGCACCC
TCACTTAATATATTTATATTTCATCATTTTTAACTTGGTAATCCTCATCGTGGG

ACCAAGGCAAAGAGAAGAGTGGTGCAGAGAGAAAAAAGAGCAGTGGGAATAGGA
TGGTTCCGTTTCTCTTCTCACCACGTCTCTCTTTTTCTCGTCACCCTTATCCT

GCTTTGTTCCTTGGGTTCTTGGGAGCAGCAGGAAGCACTATGGGCGCAGCGTCA
CGAAACAAGGAACCCAAGAACCCTCGTCGTCCTTCGTGATACCCGCGTCGCAGT

ATGACGCTGACGGTACAGGCCAGACAATTATTGTCTGGTATAGTGCAGCAGCAG
TACTGCGACTGCCATGTCCGGTCTGTTAATAACAGACCATATCACGTCGTCGTC

AACAATTTGCTGAGGGCTATTGAGGCGCAACAGCATCTGTTGCAACTCACAGTC
TTGTTAAACGACTCCCGATAACTCCGCGTTGTCGTAGACAACGTTGAGTGTCAG

TGGGGCATCAAGCAGCTCCAGGCAAGAATCCTGGCTGTGGAAAGATACCTAAAG
ACCCCGTAGTTCGTCGAGGTCCGTTCTTAGGACCGACACCTTTCTATGGATTTC

GATCAACAGCTCCTGGGGATTTGGGGTTGCTCTGGAAAACTCATTTGCACCACT
CTAGTTGTCGAGGACCCCTAAACCCCAACGAGACCTTTTGAGTAAACGTGGTGA

GCTGTGCCTTGGAATGCTAGTTGGAGTAATAAATCTCTGGAACAGATTTGGAAT
CGACACGGAACCTTACGATCAACCTCATTATTTAGAGACCTTGTCTAAACCTTA

AACATGACCTGGATGGAGTGGGACAGAGAAATTAACAATTACACA         3'
TTGTACTGGACCTACCTCACCCTGTCTCTTTAATTGTTAATGTGTTCGA
```

TABLE 8

Amino acid sequence of fusion protein R10

MetLeuArg
ProValGluThrProThrArgGluIleLysLysLeuAspGlyLeuTrpAlaPhe
SerLeuAspArgGluAsnCysGlyIleAspGlnPheProValTrpLysGluAla

TABLE 8-continued

Amino acid sequence of fusion protein R10

ThrThrThrLeuPheCysAlaSerAspAlaLysAlaTyrAspThrGluValHis
AsnValTrpAlaThrHisAlaCysValProThrAspProAsnProGlnGluVal

TABLE 8-continued

Amino acid sequence of fusion protein R10

ValLeuValAsnValThrGluAsnPheAsnMetTrpLysAsnAspMetValGlu

GlnMetHisGluAspIleIleSerLeuTrpAspGlnSerLeuLysProCysVal

LysLeuThrProLeuCysValSerLeuLysCysThrAspLeuLysAsnAspThr

AsnThrAsnSerSerSerGlyArgMetIleMetGluLysGlyGluIleLysAsn

CysSerPheAsnIleSerThrSerIleArgGlyLysValGlnLysGluTyrAla

PhePheTyrLysLeuAspIleIleProIleAspAsnAspThrThrSerTyrThr

LeuThrSerCysAsnThrSerValIleThrGlnAlaCysProLysValSerPhe

GluProIleProIleHisTyrCysAlaProAlaGlyPheAlaIleLeuLysCys

AsnAsnLysThrPheAsnGlyThrGlyProCysThrAsnValSerThrValGln

CysThrHisGlyIleArgProValValSerThrGlnLeuLeuLeuAsnGlySer

LeuAlaGluGluGluValValIleArgSerAlaAsnPheThrAspAsnAlaLys

ThrIleIleValGlnLeuAsnGlnSerValGluIleAsnCysThrArgProAsn

AsnAsnThrArgLysSerIleArgIleGlnArgGlyProGlyArgAlaPheVal

ThrIleGlyLysIleGlyAsnMetArgGlnAlaHisCysAsnIleSerArgAla

LysTrpAsnAsnThrLeuLysGlnIleAspSerLysLeuArgGluGlnPheGly

AsnAsnLysThrIleIlePheLysGlnSerSerGlyGlyAspProGluIleVal

ThrHisSerPheAsnCysGlyGlyGluPhePheTyrCysAsnSerThrGlnLeu

PheAsnSerThrTrpPheAsnSerThrTrpSerThrLysGlySerAsnAsnThr

GluGlySerAspThrIleThrLeuProCysArgIleLysGlnIleIleAsnMet

TrpGlnGluValGlyLysAlaMetTyrAlaProProIleSerGlyGlnIleArg

CysSerSerAsnIleThrGlyLeuLeuLeuThrArgAspGlyGlyAsnSerAsn

AsnGluSerGluIleHisArgSerValMetLeuTyrThrThrProAsnThrTrp

ValAspAspIleThrValValThrHisValAlaGlnAspCysAsnHisAlaSer

ValAspTrpGlnValValAlaAsnGlyAspValSerValGluLeuArgAspAla

AspGlnGlnValValAlaThrGlyGlnGlyThrSerGlyThrLeuGlnValVal

AsnProHisLeuTrpGlnProGlyGluGlyTyrLeuTyrGluLeuCysValThr

AlaLysSerGlnThrGluCysAspIleTyrProLeuArgValGlyIleArgSer

ValAlaValLysGlyGluGlnPheLeuIleAsnHisLysProPheTyrPheThr

GlyPheGlyArgHisGluAspAlaAspLeuArgGlyLysGlyPheAspAsnVal

LeuMetValHisAspHisAlaLeuMetAspTrpIleGlyAlaAsnSerTyrArg

ThrSerHisTyrProTyrAlaGluGluMetLeuAspTrpAlaAspGluHisGly

IleValValIleAspGluThrAlaAlaValGlyPheAsnLeuSerLeuGlyIle

GlyPheGluAlaGlyAsnLysProLysGluLeuTyrSerGluGluAlaValAsn

GlyGluThrGlnGlnAlaHisLeuGlnAlaIleLysGluLeuIleAlaArgAsp

LysAsnHisProSerValValMetTrpSerIleAlaAsnGluProAspThrArg

ProGlnGlyAlaArgGluTyrPheAlaProLeuAlaGluAlaThrArgLysLeu

AspProThrArgProIleThrCysValAsnValMetPheCysAspAlaHisThr

AspThrIleSerAspLeuPheAspValLeuCysLeuAsnArgTyrTyrGlyTrp

TyrValGlnSerGlyAspLeuGluThrAlaGluLysValLeuGluLysGluLeu

LeuAlaTrpGlnGluLysLeuHisGlnProIleIleIleThrGluTyrGlyVal

AspThrLeuAlaGlyLeuHisSerMetTyrThrAspMetTrpSerGluGluTyr

GlnCysAlaTrpLeuAspMetTyrHisArgValPheAspArgValSerAlaVal

ValGlyGluGlnValTrpAsnPheAlaAspPheAlaThrSerGlnGlyIleLeu

ArgValGlyGlyAsnLysLysGlyIlePheThrArgAspArgLysProLysSer

AlaAlaPheLeuLeuGlnLysArgTrpThrGlyMetAsnPheGlyGluLysPro

GlnGlnGlyGlyLysGln

TABLE 8A

Nucleotide sequence endoding fusion protein R10

```
                                                  ATGTTACGT
                                                  TACAATGCA

CCTGTAGAAACCCCAACCCGTGAAATCAAAAAACTCGACGGCCTGTGGGCATTC
GGACATCTTTGGGGTTGGGCACTTTAGTTTTTTGAGCTGCCGGACACCCGTAAG

AGTCTGGATCGCGAAAACTGTGGAATTGATCAATTCCCTGTGTGGAAGGAAGCA
TCAGACCTAGCGCTTTTGACACCTTAACTAGTTAAGGGACACACCTTCCTTCGT

ACCACCACTCTATTTTGTGCATCAGATGCTAAAGCATATGATACAGAGGTACAT
TGGTGGTGAGATAAAACACGTAGTCTACGATTTCGTATACTATGTCTCCATGTA

AATGTTTGGGCCACACATGCCTGTGTACCCACAGACCCCAACCCACAAGAAGTA
TTACAAACCCGGTGTGTACGGACACATGGGTGTCTGGGGTTGGGTGTTCTTCAT

GTATTGGTAAATGTGACAGAAAATTTTAACATGTGGAAAAATGACATGGTAGAA
CATAACCATTTACACTGTCTTTTAAAATTGTACACCTTTTTACTGTACCATCTT

CAGATGCATGAGGATATAATCAGTTTATGGGATCAAAGCCTAAAGCCATGTGTA
GTCTACGTACTCCTATATTAGTCAAATACCCTAGTTTCGGATTTCGGTACACAT

AAATTAACCCCACTCTGTGTTAGTTTAAAGTGCACTGATTTGAAGAATGATACT
TTTAATTGGGGTGAGACACAATCAAATTTCACGTGACTAAACTTCTTACTATGA

AATACCAATAGTAGTAGCGGGAGAATGATAATGGAGAAAGGAGAGATAAAAAAC
TTATGGTTATCATCATCGCCCTCTTACTATTACCTCTTTCCTCTCTATTTTTTG

TGCTCTTTCAATATCAGCACAAGCATAAGAGGTAAGGTGCAGAAAGAATATGCA
ACGAGAAAGTTATAGTCGTGTTCGTATTCTCCATTCCACGTCTTTCTTATACGT
```

-continued

```
TTTTTTTATAAACTTGATATAATACCAATAGATAATGATACTACCAGCTATACG
AAAAAAATATTTGAACTATATTATGGTTATCTATTACTATGATGGTCGATATGC

TTGACAAGTTGTAACACCTCAGTCATTACACAGGCCTGTCCAAAGGTATCCTTT
AACTGTTCAACATTGTGGAGTCAGTAATGTGTCCGGACAGGTTTCCATAGGAAA

GAGCCAATTCCCATACATTATTGTGCCCCGGCTGGTTTTGCGATTCTAAAATGT
CTCGGTTAAGGGTATGTAATAACACGGGGCCGACCAAAACGCTAAGATTTTACA

AATAATAAGACGTTCAATGGAACAGGACCATGTACAAATGTCAGCACAGTACAA
TTATTATTCTGCAAGTTACCTTGTCCTGGTACATGTTTACAGTCGTGTCATGTT

TGTACACATGGAATTAGGCCAGTAGTATCAACTCAACTGCTGTTAAATGGCAGT
ACATGTGTACCTTAATCCGGTCATCATAGTTGAGTTGACGACAATTTACCGTCA

CTAGCAGAAGAAGAGGTAGTAATTAGATCTGCCAATTTCACAGACAATGCTAAA
GATCGTCTTCTTCTCCATCATTAATCTAGACGGTTAAAGTGTCTGTTACGATTT

ACCATAATAGTACAGCTGAACCAATCTGTAGAAATTAATTGTACAAGACCCAAC
TGGTATTATCATGTCGACTTGGTTAGACATCTTTAATTAACATGTTCTGGGTTG

AACAATACAAGAAAAAGTATCCGTATCCAGAGAGGACCAGGGAGAGCATTTGTT
TTGTTATGTTCTTTTTCATAGGCATAGGTCTCTCCTAATCCCTCTCGTAAACAA

ACAATAGGAAAAATAGGAAATATGAGACAAGCACATTGTAACATTAGTAGAGCA
TGTTATCCTTTTTATCCTTTATACTCTGTTCGTGTAACATTGTAATCATCTCGT

AAATGGAATAACACTTTAAAACAGATAGATAGCAAATTAAGAGAACAATTTGGA
TTTACCTTATTGTGAAATTTTGTCTATCTATCGTTTAATTCTCTTGTTAAACCT

AATAATAAAACAATAATCTTTAAGCAGTCCTCAGGAGGGGACCCAGAAATTGTA
TTATTATTTTGTTATTAGAAATTCGTCAGGAGTCCTCCCCTGGGTCTTTAACAT

ACGCACAGTTTTAATTGTGGAGGGGAATTTTTCTACTGTAATTCAACACAACTG
TGCGTGTCAAAATTAACACCTCCCCTTAAAAAGATGACATTAAGTTGTGTTGAC

TTTAATAGTACTTGGTTTAATAGTACTTGGAGTACTAAAGGGTCAAATAACACT
AAATTATCATGAACCAAATTATCATGAACCTCATGATTTCCCAGTTTATTGTGA

GAAGGAAGTGACACAATCACCCTCCCATGCAGAATAAAACAAATTATAAACATG
CTTCCTTCACTGTGTTAGTGGGAGGGTACGTCTTATTTTGTTTAATATTTGTAC

TGGCAGGAAGTAGGAAAAGCAATGTATGCCCCTCCCATCAGTGGACAAATTAGA
ACCGTCCTTCATCCTTTTCGTTACATACGGGGAGGGTAGTCACCTGTTTAATCT

TGTTCATCAAATATTACAGGGCTGCTATTAACAAGAGATGGTGGTAATAGCAAC
ACAAGTAGTTTATAATGTCCCGACGATAATTGTTCTCTACCACCATTATCGTTG

AATGAGTCCGAGATCCATCGCAGCGTAATGCTCTACACCACGCCGAACACCTGG
TTACTCAGGCTCTAGGTAGCGTCGCATTACGAGATGTGGTGCGGCTTGTGGACC

GTGGACGATATCACCGTGGTGACGCATGTCGCGCAAGACTGTAACCACGCGTCT
CACCTGCTATAGTGGCACCACTGCGTACAGCGCGTTCTGACATTGGTGCGCAGA

GTTGACTGGCAGGTGGTGGCCAATGGTGATGTCAGCGTTGAACTGCGTGATGCG
CAACTGACCGTCCACCACCGGTTACCACTACAGTCGCAACTTGACGCACTACGC

GATCAACAGGTGGTTGCAACTGGACAAGGCACTAGCGGGACTTTGCAAGTGGTG
CTAGTTGTCCACCAACGTTGACCTGTTCCGTGTATCGCCCTGAAACGTTCACCA

AATCCGCACCTCTGGCAACCGGGTGAAGGTTATCTCTATGAACTGTGCGTCACA
TTAGGCGTGGAGACCGTTGGCCCACTTCCAATAGAGATACTTGACACGCAGTGT

GCCAAAGCCAGACAGAGTGTGATATCTACCCGCTTCGCGTCGGCATCCGGTCA
CGGTTTTCGGTCTGTCTCACACTATAGATGGGCGAAGCGCAGCCGTAGGCCAGT

GTGGCAGTGAAGGGCGAACAGTTCCTGATTAACCACAAACCGTTCTACTTTACT
CACCGTCACTTCCCGCTTGTCAAGGACTAATTGGTGTTTGGCAAGATGAAATGA

GGCTTTGGTCGTCATGAAGATGCGGACTTGCGTGGCAAAGGATTCGATAACGTG
CCGAAACCAGCAGCACTTCTACGCCTGAACGCACCGTTTCCTAAGCTATTGCAC

CTGATGGTGCACGACCACGCATTAATGGACTGGATTGGGGCCAACTCCTACCGT
GACTACCACGTGCTGGTGCGTAATTACCTGACCTAACCCCGGTTGAGGATGGCA

ACCTCGCATTACCCTTACGCTGAAGAGATGCTCGACTGGGCAGATGAACATGGC
TGGAGCGTAATGGGAATGCGACTTCTCTACGAGCTGACCCGTCTACTTGTACCG

ATCGTGGTGATTGATGAAACTGCTGCTGTCGGCTTTAACCTCTCTTTAGGCATT
TAGCACCACTAACTACTTTGACGACGACAGCCGAAATTGGAGAGAAATCCGTAA
```

-continued

```
GGTTTCGAAGCGGGCAACAAGCCGAAAGAACTGTACAGCGAAGAGGCAGTCAAC
CCAAAGCTTCGCCCGTTGTTCGGCTTTCTTGACATGTCGCTTCTCCGTCAGTTG

GGGGAAACTCAGCAAGCGCACTTACAGGCGATTAAAGAGCTGATAGCGCGTGAC
CCCCTTTGAGTCGTTCGCGTGAATGTCCGCTAATTTCTCGACTATCGCGCACTG

AAAAACCACCCAAGCGTGGTGATGTGGAGTATTGCCAACGAACCGGATACCCGT
TTTTTGGTGGGTTCGCACCACTACACCTCATAACGGTTGCTTGGCCTATGGGCA

CCGCAAGGTGCACGGGAATATTTCGCGCCACTGGCGGAAGCAACGCGTAAACTC
GGCGTTCCACGTGCCCTTATAAAGCGCGGTGACCGCCTTCGTTGCGCATTTGAG

GACCCGACGCGTCCGATCACCTGCGTCAATGTAATGTTCTGCGACGCTCACACC
CTGGGCTGCGCAGGCTAGTGGACGCAGTTACATTACAAGACGCTGCGAGTGTGG

GATACCATCAGCGATCTCTTTGATGTGCTGTGCCTGAACCGTTATTACGGATGG
CTATGGTAGTCGCTAGAGAAACTACACGACACGGACTTGGCAATAATGCCTACC

TATGTCCAAAGCGGCGATTTGGAAACGGCAGAGAAGGTACTGGAAAAAGAACTT
ATACAGGTTTCGCCGCTAAACCTTTGCCGTCTCTTCCATGACCTTTTTCTTGAA

CTGGCCTGGCAGGAGAAACTGCATCAGCCGATTATCATCACCGAATACGGCGTG
GACCGGACCGTCCTCTTTGACGTAGTCGGCTAATAGTAGTGGCTTATGCCGCAC

GATACGTTAGCCGGGCTGCACTCAATGTACACCGACATGTGGAGTGAAGAGTAT
CTATGCAATCGGCCCGACGTGAGTTACATGTGGCTGTACACCTCACTTCTCATA

CAGTGTGCATGGCTGGATATGTATCACCGCGTCTTTGATCGCGTCAGCGCCGTC
GTCACACGTACCGACCTATACATAGTGGCGCAGAAACTAGCGCAGTCGCGGCAG

GTCGGTGAACAGGTATGGAATTTCGCCGATTTTGCGACCTCGCAAGGCATATTG
CAGCCACTTGTCCATACCTTAAAGCGGCTAAAACGCTGGAGCGTTCCGTATAAC

CGCGTTGGCGGTAACAAGAAAGGGATCTTCACTCGCGACCGCAAACCGAAGTCG
GCGCAACCGCCATTGTTCTTTCCCTAGAAGTGAGCGCTGGCGTTTGGCTTCAGC

GCGGCTTTTCTGCTGCAAAAACGCTGGACTGGCATGAACTTCGGTGAAAAACCG
CGCCGAAAAGACGACGTTTTTGCGACCTGACCGTACTTGAAGCCACTTTTTGGC

CAGCAGGGAGGCAAACAA
GTCGTCCCTCCGTTTGTT
```

TABLE 9

| Amino acid sequence of fusion protein PB1 |
|---|
| MetLeuArg |
| ProValGluThrProThrArgGluIleLysLysLeuAspGlyLeuTrpAlaPhe |
| SerLeuAspArgGluArgValAlaAspLeuAsnGlnSerValGluIleAsnCys |
| ThrArgProAsnAsnAsnThrArgLysSerIleArgIleGlnArgGlyProGly |
| ArgAlaPheValThrIleGlyLysIleGlyAsnMetArgGlnAlaHisCysAsn |
| IleSerArgAlaLysTrpAsnAsnThrLeuLysGlnIleAspSerLysLeuArg |
| GluGlnPheGlyAsnAsnLysThrIleIlePheLysGlnSerSerGlyGlyAsp |
| ProGluIleValThrHisSerPheAsnCysGlyGlyGluPhePheTyrCysAsn |
| SerThrGlnLeuPheAsnSerThrTrpPheAsnSerThrTrpSerThrLysGly |
| SerAsnAsnThrGluGlySerAspThrIleThrLeuProCysArgIleLysGln |
| IleIleAsnMetTrpGlnGluValGlyLysAlaMetTyrAlaProProIleSer |
| GlyGlnIleArgCysSerSerAsnIleThrGlyLeuLeuLeuThrArgAspGly |
| GlyAsnSerAsnAsnGluSerGluIleArgArgGlnAlaSerArgGluLeuGlu |
| PheLeuLysThrLysGlyProArgAspThrProIlePheIleGly |

TABLE 9A

| Nucleotide sequence encoding fusion protein PB1 |
|---|
| ATGTTACGTCCTGTAGAAACCCCAACCCGTGAAATCAAAAAACTCGACGGCCTG |
| TACAATGCAGGACATCTTTGGGGTTGGGCACTTTAGTTTTTTGAGCTGCCGGAC |
| TGGGCATTCAGTCTGGATCGCGAACGCGTGGCCGATCTGAACCAATCTGTAGAA |
| ACCCGTAAGTCAGACCTAGCGCTTGCGCACCGGCTAGACTTGGTTAGACATCTT |
| ATTAATTGTACAAGACCCAACAACAATACAAGAAAAAGTATCCGTATCCAGAGA |
| TAATTAACATGTTCTGGGTTGTTGTTATGTTCTTTTTCATAGGCATAGGTCTCT |
| GGACCAGGGAGAGCATTTGTTACAATAGGAAAAATAGGAAATATGAGACAAGCA |
| CCTAATCCCTCTCGTAAACAATGTTATCCTTTTTATCCTTTATACTCTGTTCGT |
| CATTGTAACATTAGTAGAGCAAAATGGAATAACACTTTAAAACAGATAGATAGC |
| GTAACATTGTAATCATCTCGTTTTACCTTATTGTGAAATTTGTCTATCTATCG |
| AAATTAAGAGAACAATTTGGAAATAATAAAACAATAATCTTTAAGCAGTCCTCA |
| TTTAATTCTCTTGTTAAACCTTTATTATTTTGTTATTAGAAATTCGTCAGGAGT |

TABLE 9A-continued
Nucleotide sequence encoding fusion protein PB1

GGAGGGGACCCAGAAATTGTAACGCACAGTTTTAATTGTGGAGGGGAATTTTTC
CCTCCCCTGGGTCTTTAACATTGCGTGTCAAAATTAACACCTCCCCTTAAAAAG

TACTGTAATTCAACACAACTGTTTAATAGTACTTGGTTTAATAGTACTTGGAGT
ATGACATTAAGTTGTGTTGACAAATTATCATGAACCAAATTATCATGAACCTCA

ACTAAAGGGTCAAATAACACTGAAGGAAGTGACACAATCACCCTCCCATGCAGA
TGATTTCCCAGTTTATTGTGACTTCCTTCACTGTGTTAGTGGGAGGGTACGTCT

ATAAAACAAATTATAAACATGTGGCAGGAAGTAGGAAAAGCAATGTATGCCCCT
TATTTTGTTTAATATTTGTACACCGTCCTTCATCCTTTTCGTTACATACGGGGA

CCCATCAGTGGACAAATTAGATGTTCATCAAATATTACAGGGCTGCTATTAACA
GGGTAGTCACCTGTTTAATCTACAAGTAGTTTATAATGTCCCGACGATAATTGT

AGAGATGGTGGTAATAGCAACAATGAGTCCGAGATCCGTCGACAAGCTTCCCGG
TCTCTACCACCATTATCGTTGTTACTCAGGCTCTAGGCAGCTGTTCGAAGGGCC

GAGCTCGAATTCTTGAAGACGAAAGGGCCTCGTGATACTCCTATTTTTATAGGT
CTCGAGCTTAAGAACTTCTGCTTTCCCGGAGCACTATGCGGATAAAAATATCCA

TABLE 10
Amino acid sequence of fusion protein 590

MetLeuArgProValGluThr
ProThrArgGluIleLysLysLeuAspGlyLeuTrpAlaPheSerLeuAspArg
GluArgValAlaAspLeuAsnGlnSerValGluIleAsnCysThrArgProAsn
AsnAsnThrArgLysSerIleArgIleGlnArgGlyProGlyArgAlaPheVal
ThrIleGlyLysIleGlyAsnMetArgGlnAlaHisCysAsnIleSerArgAla
LysTrpAsnAsnThrLeuLysGlnIleAspSerLysLeuArgGluGlnPheGly
AsnAsnLysThrIleIlePheLysGlnSerSerGlyGlyAspProGluIleVal
ThrHisSerPheAsnCysGlyGlyGluPhePheTyrCysAsnSerThrGlnLeu
PheAsnSerThrTrpPheAsnSerThrTrpSerThrLysGlySerAsnAsnThr
GluGlySerAspThrIleThrLeuProCysArgIleLysGlnIleIleAsnMet
TrpGlnGluValGlyLysAlaMetTyrAlaProProIleSerGlyGlnIleArg
CysSerSerAsnIleThrGlyLeuLeuLeuThrArgAspGlyGlyAsnSerAsn
AsnGluSerGluIlePheArgProGlyGlyGlyAspMetArgAspAsnTrpArg
SerGluLeuTyrLysTyrLysValValLysIleGluProLeuGlyValAlaPro
ThrLysAlaLysArgArgValValGlnArgGluLysArgAlaValGlyIleGly
AlaLeuPheLeuGlyPheLeuGlyAlaAlaGlySerThrMetGlyAlaAlaSer
MetThrLeuThrValGlnAlaArgGlnLeuLeuSerGlyIleValGlnGlnGln
AsnAsnLeuLeuArgAlaIleGluAlaGlnGlnHisLeuLeuGlnLeuThrVal
TrpGlyIleLysGlnLeuGlnAlaArgIleLeuAlaValGluArgTyrLeuLys
AspGlnGlnLeuLeuGlyIleTrpGlyCysSerGlyLysLeuIleCysThrThr
AlaValProTrpAsnAlaSerTrpSerAsnLysSerLeuGluGlnIleTrpAsn
AsnMetThrTrpMetGluTrpAspArgGluIleAsnAsnTyrThrSerPhePro
IleHisArgSerValMetLeuTyrThrThrProAsnThrTrpValAspAspIle
ThrValValThrHisValAlaGlnAspCysAsnHisAlaSerValAspTrpGln
ValValAlaAsnGlyAspValSerValGluLeuArgAspAlaAspGlnGlnVal
ValAlaThrGlyGlnGlyThrSerGlyThrLeuGlnValValAsnProHisLeu
TrpGlnProGlyGluGlyTyrLeuTyrGluLeuCysValThrAlaLysSerGln
ThrGluCysAspIleTyrProLeuArgValGlyIleArgSerValAlaValLys
GlyGluGlnPheLeuIleAsnHisLysProPheTyrPheThrGlyPheGlyArg
HisGluAspAlaAspLeuArgGlyLysGlyPheAspAsnValLeuMetValHis
AspHisAlaLeuMetAspTrpIleGlyAlaAsnSerTyrArgThrSerHisTyr
ProTyrAlaGluGluMetLeuAspTrpAlaAspGluHisGlyIleValValIle
AspGluThrAlaAlaValGlyPheAsnLeuSerLeuGlyIleGlyPheGluAla
GlyAsnLysProLysGluLeuTyrSerGluGluAlaValAsnGlyGluThrGln
GlnAlaHisLeuGlnAlaIleLysGluIleAlaArgAspLysAsnHisPro
SerValValMetTrpSerIleAlaAsnGluProAspThrArgProGlnGlyAla
ArgGluTyrPheAlaProLeuAlaGluAlaThrArgLysLeuAspProThrArg
ProIleThrCysValAsnValMetPheCysAspAlaHisThrAspThrIleSer
AspLeuPheAspValLeuCysLeuAsnArgTyrTyrGlyTrpTyrValGlnSer
GlyAspLeuGluThrAlaGluLysValLeuGluLysGluLeuLeuAlaTrpGln
GluLysLeuHisGlnProIleIleIleThrGluTyrGlyValAspThrLeuAla
GlyLeuHisSerMetTyrThrAspMetTrpSerGluGluTyrGlnCysAlaTrp
LeuAspMetTyrHisArgValPheAspArgValSerAlaValValGlyGluGln
ValTrpAsnPheAlaAspPheAlaThrSerGlnGlyIleLeuArgValGlyGly
AsnLysLysGlyIlePheThrArgAspArgLysProLysSerAlaAlaPheLeu
LeuGlnLysArgTrpThrGlyMetAsnPheGlyGluLysProGlnGlnGlyGly
LysGln

TABLE 10A
Nucleotide sequence encoding fusion protein 590

ATGTTACGTCCTGTAGAAACC

```
                                           TACAATGCAGGACATCTTTGG

CCAACCCGTGAAATCAAAAAACTCGACGGCCTGTGGGCATTCAGTCTGGATCGC
GGTTGGGCACTTTAGTTTTTTGAGATGCCGGACACCCGTAAGTCAGACCTAGCG

GAACGCGTGGCCGATCTGAACCAATCTGTAGAAATTAATTGTACAAGACCCAAC
CTTGCGCACCGGCTAGACTTGGTTAGACATCTTTAATTAACATGTTCTGGGTTG

AACAATACAAGAAAAAGTATCCGTATCCAGAGAGGACCAGGGAGAGCATTTGTT
TTGTTATGTTCTTTTTCATAGGCATAGGTCTCTCCTAATCCCTCTCGTAAACAA

ACAATAGGAAAAATAGGAAATATGAGACAAGCACATTGTAACATTAGTAGAGCA
TGTTATCCTTTTTATCCTTTATACTCTGTTCGTGTAACATTGTAATCATCTCGT

AAATGGAATAACACTTTAAAACAGATAGATAGCAAATTAAGAGAACAATTTGGA
TTTACCTTATTGTGAAATTTTGTCTATCTATCGTTTAATTCTCTTGTTAAACCT

AATAATAAAACAATAATCTTTAAGCAGTCCTCAGGAGGGGACCCAGAAATTGTA
TTATTATTTTGTTATTAGAAATTCGTCAGGAGTCCTCCCCTGGGTCTTTAACAT

ACGCACAGTTTTAATTGTGGAGGGGAATTTTTCTACTGTAATTCAACACAACTG
TGCGTGTCAAAATTAACACCTCCCCTTAAAAAGATGACATTAAGTTGTGTTGAC

TTTAATAGTACTTGGTTTAATAGTACTTGGAGTACTAAAGGGTCAAATAACACT
AAATTATCATGAACCAAATTATCATGAACCTCATGATTTCCCAGTTTATTGTGA

GAAGGAAGTGACACAATCACCCTCCCATGCAGAATAAAACAAATTATAAACATG
CTTCCTTCACTGTGTTAGTGGGAGGGTACGTCTTATTTTGTTTAATATTTGTAC

TGGCAGGAAGTAGGAAAAGCAATGTATGCCCCTCCCATCAGTGGACAAATTAGA
ACCGTCCTTCATCCTTTTCGTTACATACGGGGAGGGTAGTCACCTGTTTAATCT

TGTTCATCAAATATTACAGGGCTGCTATTAACAAGAGATGGTGGTAATAGCAAC
ACAAGTAGTTTATAATGTCCCGACGATAATTGTTCTCTACCACCATTATCGTTG

AATGAGTCCGAGATCTTCAGACCTGGAGGAGGAGATATGAGGGACAATTGGAGA
TTACTCAGGCTCTAGAAGTCTGGACCTCCTCCTCTATACTCCCTGTTAACCTCT

AGTGAATTATATAAATATAAAGTAGTAAAAATTGAACCATTAGGAGTAGCACCC
TCACTTAATATATTTATATTTCATCATTTTTAACTTGGTAATCCTCATCGTGGG

ACCAAGGCAAAGAGAAGAGTGGTGCAGAGAGAAAAAGAGCAGTGGGAATAGGA
TGGTTCCGTTTCTCTTCTCACCACGTCTCTCTTTTTTCTCGTCACCCTTATCCT

GCTTTGTTCCTTGGGTTCTTGGGAGCAGCAGGAAGCACTATGGGCGCAGCGTCA
CGAAACAAGGAACCCAAGAACCCTCGTCGTCCTTCGTGATACCCGCGTCGCAGT

ATGACGCTGACGGTACAGGCCAGACAATTATTGTCTGGTATAGTGCAGCAGCAG
TACTGCGACTGCCATGTCCGGTCTGTTAATAACAGACCATATCACGTCGTCGTC

AACAATTTGCTGAGGGCTATTGAGGCGCAACAGCATCTGTTGCAACTCACAGTC
TTGTTAAACGACTCCCGATAACTCCGCGTTGTCGTAGACAACGTTGAGTGTCAG

TGGGGCATCAAGCAGCTCCAGGCAAGAATCCTGGCTGTGGAAAGATACCTAAAG
ACCCCGTAGTTCGTCGAGGTCCGTTCTTAGGACCGACACCTTTCTATGGATTTC

GATCAACAGCTCCTGGGGATTTGGGGTTGCTCTGGAAAACTCATTTGCACCACT
CTAGTTGTCGAGGACCCCTAAACCCCAACGAGACCTTTTGAGTAAACGTGGTGA

GCTGTGCCTTGGAATGCTAGTTGGAGTAATAAATCTCTGGAACAGATTTGGAAT
CGACACGGAACCTTACGATCAACCTCATTATTTAGAGACCTTGTCTAAACCTTA

AACATGACCTGGATGGAGTGGGACAGAGAAATTAACAATTACACAAGCTTCCCG
TTGTACTGGACCTACCTCACCCTGTCTCTTTAATTGTTAATGTGTTCGAAGGGC

ATCCATCGCAGCGTAATGCTCTACACCACGCCGAACACCTGGGTGGACGATATC
TAGGTAGCGTCGCATTACGAGATGTGGTGCGGCTTGTGGACCCACCTGCTATAG

ACCGTGGTGACGCATGTCGCGCAAGACTGTAACCACGCGTCTGTTGACTGGCAG
TGGCACCACTGCGTACAGCGCGTTCTGACATTGGTGCGCAGACAACTGACCGTC

GTGGTGGCCAATGGTGATGTCAGCGTTGAACTGCGTGATGCGGATCAACAGGTG
CACCACCGGTTACCACTACAGTCGCAACTTGACGCACTACGCCTAGTTGTCCAC

GTTGCAACTGGACAAGGCACTAGCGGGACTTTGCAAGTGGTGAATCCGCACCTC
CAACGTTGACCTGTTCCGTGATCGCCCTGAAACGTTCACCACTTAGGCGTGGAG

TGGCAACCGGGTGAAGGTTATCTCTATGAACTGTGCGTCACAGCCAAAAGCCAG
ACCGTTGGCCCACTTCCAATAGAGATACTTGACACGCAGTGTCGGTTTTCGGTC

ACAGAGTGTGATATCTACCCGCTTCGCGTCGGCATCCGGTCAGTGGCAGTGAAG
TGTCTCACACTATAGATGGGCGAAGCGCAGCCGTAGGCCAGTCACCGTCACTTC
```

-continued

```
GGCGAACAGTTCCTGATTAACCACAAACCGTTCTACTTTACTGGCTTTGGTCGT
CCGCTTGTCAAGGACTAATTGGTGTTTGGCAAGATGAAATGACCGAAACCAGCA

CATGAAGATGCGGACTTGCGTGGCAAAGGATTCGATAACGTGCTGATGGTGCAC
GCACTTCTACGCCTGAACGCACCGTTTCCTAAGCTATTGCACGACTACCACGTG

GACCACGCATTAATGGACTGGATTGGGGCCAACTCCTACCGTACCTCGCATTAC
CTGGTGCGTAATTACCTGACCTAACCCCGGTTGAGGATGGCATGGAGCGTAATG

CCTTACGCTGAAGAGATGCTCGACTGGGCAGATGAACATGGCATCGTGGTGATT
GGAATGCGACTTCTCTACGAGCTGACCCGTCTACTTGTACCGTAGCACCACTAA

GATGAAACTGCTGCTGTCGGCTTTAACCTCTCTTTAGGCATTGGTTTCGAAGCG
CTACTTTGACGACGACAGCCGAAATTGGAGAGAAATCCGTAACCAAAGCTTCGC

GGCAACAAGCCGAAAGAACTGTACAGCGAAGAGGCAGTCAACGGGGAAACTCAG
CCGTTGTTCGGCTTTCTTGACATGTCGCTTCTCCGTCAGTTGCCCCTTTGAGTC

CAAGCGCACTTACAGGCGATTAAAGAGCTGATAGCGCGTGACAAAAACCACCCA
GTTCGCGTGAATGTCCGCTAATTTCTCGACTATCGCGCACTGTTTTTGGTGGGT

AGCGTGGTGATGTGGAGTATTGCCAACGAACCGGATACCCGTCCGCAAGGTGCA
TCGCACCACTACACCTCATAACGGTTGCTTGGCCTATGGGCAGGCGTTCCACGT

CGGGAATATTTCGCGCCACTGGCGGAAGCAACGCGTAAACTCGACCCGACGCGT
GCCCTTATAAAGCGCGGTGACCGCCTTCGTTGCGCATTTGAGCTGGGCTGCGCA

CCGATCACCTGCGTCAATGTAATGTTCTGCGACGCTCACACCGATACCATCAGC
GGCTAGTGGACGCAGTTACATTACAAGACGCTGCGAGTGTGGCTATGGTAGTCG

GATCTCTTTGATGTGCTGTGCCTGAACCGTTATTACGGATGGTATGTCCAAAGC
CTAGAGAAACTACACGACACGGACTTGGCAATAATGCCTACCATACAGGTTTCG

GGCGATTTGGAAACGGCAGAGAAGGTACTGGAAAAAGAACTTCTGGCCTGGCAG
CCGCTAAACCTTTGCCGTCTCTTCCATGACCTTTTTCTTGAAGACCGGACCGTC

GAGAAACTGCATCAGCCGATTATCATCACCGAATACGGCGTGGATACGTTAGCC
CTCTTTGACGTAGTCGGCTAATAGTAGTGGCTTATGCCGCACCTATGCAATCGG

GGGCTGCACTCAATGTACACCGACATGTGGAGTGAAGAGTATCAGTGTGCATGG
CCCGACGTGAGTTACATGTGGCTGTACACCTCACTTCTCATAGTCACACGTACC

CTGGATATGTATCACCGCGTCTTTGATCGCGTCAGCGCCGTCGTCGGTGAACAG
GACCTATACATAGTGGCGCAGAAACTAGCGCAGTCGCGGCAGCAGCCACTTGTC

GTATGGAATTTCGCCGATTTTGCGACCTCGCAAGGCATATTGCGCGTTGGCGGT
CATACCTTAAAGCGGCTAAAACGCTGGAGCGTTCCGTATAACGCGCAACCGCCA

AACAAGAAAGGGATCTTCACTCGCGACCGCAAACCGAAGTCGGCGGCTTTTCTG
TTGTTCTTTCCCTAGAAGTGAGCGCTGGCGTTTGGCTTCAGCCGCCGAAAAGAC

CTGCAAAAACGCTGGACTGGCATGAACTTCGGTGAAAAACCGCAGCAGGGAGGC
GACGTTTTTGCGACCTGACCGTACTTGAAGCCACTTTTTGGCGTCGTCCCTCCG

AAACAA
TTTGTT
```

TABLE 11
Amino acid sequence of fusion protein KH1

MetLeuArg
ProValGluThrProThrArgGluIleLysLysLeuAspGlyLeuTrpAlaPhe
SerLeuAspArgGluArgGluPheProValTrpLysGluAlaThrThrThrLeu
PheCysAlaSerAspAlaLysAlaTyrAspThrGluValHisAsnValTrpAla
ThrHisAlaCysValProThrAspProAsnProGlnGluValValLeuValAsn
ValThrGluAsnPheAsnMetTrpLysAsnAspMetValGluGlnMetHisGlu
AspIleIleSerLeuTrpAspGlnSerLeuLysProCysValLysLeuThrPro
LeuCysValSerLeuLysCysThrAspLeuLysAsnAspThrAsnThrAsnSer
SerSerGlyArgMetIleMetGluLysGlyGluIleLysAsnCysSerPheAsn
IleSerThrSerIleArgGlyLysValGlnLysGluTyrAlaPhePheTyrLys
LeuAspIleIleProIleAspAsnAspThrThrSerTyrThrLeuThrSerCys
AsnThrSerValIleThrGlnAlaCysProLysValSerPheGluProIlePro
IleHisTyrCysAlaProAlaGlyPheAlaIleLeuLysCysAsnAsnLysThr
PheAsnGlyThrGlyProCysThrAsnValSerThrValGlnCysThrHisGly
IleArgProValValSerThrGlnLeuLeuLeuAsnGlySerLeuAlaGluGlu
GluValValIleArgSerAlaAsnPheThrAspAsnAlaLysThrIleIleVal
GlnLeuAsnGlnSerValGluIleAsnCysThrArgProAsnAsnAsnThrArg
LysSerIleArgIleGlnArgGlyProGlyArgAlaPheValThrIleGlyLys
IleGlyAsnMetArgGlnAlaHisCysAsnIleSerArgAlaLysTrpAsnAsn

TABLE 11-continued

Amino acid sequence of fusion protein KH1

ThrLeuLysGlnIleAspSerLysLeuArgGluGlnPheGlyAsnAsnLysThr
IleIlePheLysGlnSerSerGlyGlyAspProGluIleValThrHisSerPhe
AsnCysGlyGlyGluPhePheTyrCysAsnSerThrGlnLeuPheAsnSerThr
TrpPheAsnSerThrTrpSerThrLysGlySerAsnAsnThrGluGlySerAsp
ThrIleThrLeuProCysArgIleLysGlnIleIleAsnMetTrpGlnGluVal
GlyLysAlaMetTyrAlaProProIleSerGlyGlnIleArgCysSerSerAsn
IleThrGlyLeuLeuLeuThrArgAspGlyGlyAsnSerAsnAsnGluSerGlu
IlePheArgProGlyGlyGlyAspMetArgAspAsnTrpArgSerGluLeuTyr
LysTyrLysValValLysIleGluProLeuGlyValAlaProThrLysAlaLys
ArgArgValValGlnArgGluLysArgAlaValGlyIleGlyAlaLeuPheLeu
GlyPheLeuGlyAlaAlaGlySerThrMetGlyAlaAlaSerMetThrLeuThr
ValGlnAlaArgGlnLeuLeuSerGlyIleValGlnGlnGlnAsnAsnLeuLeu
ArgAlaIleGluAlaGlnGlnHisLeuLeuGlnLeuThrValTrpGlyIleLys
GlnLeuGlnAlaArgIleLeuAlaValGluArgTyrLeuLysAspGlnGlnLeu
LeuGlyIleTrpGlyCysSerGlyLysLeuIleCysThrThrAlaValProTrp
AsnAlaSerTrpSerAsnLysSerLeuGluGlnIleTrpAsnAsnMetThrTrp
MetGluTrpAspArgGluIleAsnAsnTyrThrSerPheProGlyAlaArgIle
LeuGluAspGluArgAlaSer

TABLE 11A

Nucleotide sequence encoding fusion protein KH1

```
                                               ATGTTACGT
                                               TACAATGCA

CCTGTAGAAACCCCAACCCGTGAAATCAAAAAACTCGACGGCCTGTGGGCATTC
GGACATCTTTGGGGTTGGGCACTTTAGTTTTTTGAGCTGCCGGACACCCGTAAG

AGTCTGGATCGCGAACGCGAATTCCCTGTGTGGAAGGAAGCAACCACCACTCTA
TCAGACCTAGCGCTTGCGCTTAAGGGACACACCTTCCTTCGTTGGTGGTGAGAT

TTTTGTGCATCAGATGCTAAAGCATATGATACAGAGGTACATAATGTTTGGGCC
AAAACACGTAGTCTACGATTTCGTATACTATGTCTCCATGTATTACAAACCCGG

ACACATGCCTGTGTACCCACAGACCCCAACCCACAAGAAGTAGTATTGGTAAAT
TGTGTACGGACACATGGGTGTCTGGGGTTGGGTGTTCTTCATCATAACCATTTA

GTGACAGAAAATTTTAACATGTGGAAAAATGACATGGTAGAACAGATGCATGAG
CACTGTCTTTTAAAATTGTACACCTTTTTACTGTACCATCTTGTCTACGTACTC

GATATAATCAGTTTATGGGATCAAAGCCTAAAGCCATGTGTAAAATTAACCCCA
CTATATTAGTCAAATACCCTAGTTTCGGATTTCGGTACACATTTTAATTGGGGT

CTCTGTGTTAGTTTAAAGTGCACTGATTTGAAGAATGATACTAATACCAATAGT
GAGACACAATCAAATTTCACGTGACTAAACTTCTTACTATGATTATGGTTATCA

AGTAGCGGGAGAATGATAATGGAGAAAGGAGAGATAAAAAACTGCTCTTTCAAT
TCATCGCCCTCTTACTATTACCTCTTTCCTCTCTATTTTTTGACGAGAAAGTTA

ATCAGCACAAGCATAAGAGGTAAGGTGCAGAAAGAATATGCATTTTTTTATAAA
TAGTCGTGTTCGTATTCTCCATTCCACGTCTTTCTTATACGTAAAAAAATATTT

CTTGATATAATACCAATAGATAATGATACTACCAGCTATACGTTGACAAGTTGT
GAACTATATTATGGTTATCTATTACTATGATGGTCGATATGCAACTGTTCAACA

AACACCTCAGTCATTACACAGGCTTGTCCAAAGGTATCCTTTGAGCCAATTCCC
TTGTGGAGTCAGTAATGTGTCCGGACAGGTTTCCATAGGAAACTCGGTTAAGGG

ATACATTATTGTGCCCCGGCTGGTTTTGCGATTCTAAAATGTAATAATAAGACG
TATGTAATAACACGGGGCCGACCAAAACGCTAAGATTTTACATTATTATTCTGC

TTCAATGGAACAGGACCATGTACAAATGTCAGCACAGTACAATGTACACATGGA
AAGTTACCTTGTCCTGGTACATGTTTACAGTCGTGTCATGTTACATGTGTACCT

ATTAGGCCAGTAGTATCAACTCAACTGCTGTTAAATGGCAGTCTAGCAGAAGAA
TAATCCGGTCATCATAGTTGAGTTGACGACAATTTACCGTCAGATCGTCTTCTT

GAGGTAGTAATTAGATCTGCCAATTTCACAGACAATGCTAAAACCATAATAGTA
CTCCATCATTAATCTAGACGGTTAAAGTGTCTGTTACGATTTTGGTATTATCAT

CAGCTGAACCAATCTGTAGAAATTAATTGTACAAGACCCAACAACAATACAAGA
GTCGACTTGGTTAGACATCTTTAATTAACATGTTCTGGGTTGTTGTTATGTTCT

AAAAGTATCCGTATCCAGAGAGGACCAGGGAGAGCATTTGTTACAATAGGAAAA
TTTTCATAGGCATAGGTCTCTCCTGGTCCCTCTCGTAAACAATGTTATCCTTTT

ATAGGAAATATGAGACAAGCACATTGTAACATTAGTAGAGCAAAATGGAATAAC
TATCCTTTATACTCTGTTCGTGTAACATTGTAATCATCTCGTTTTACCTTATTG
```

TABLE 11A-continued

| Nucleotide sequence encoding fusion protein KH1 |
|---|
| ACTTTAAAACAGATAGATAGCAAATTAAGAGAACAATTTGGAAATAATAAAACA<br>TGAAATTTTGTCTATCTATCGTTTAATTCTCTTGTTAAACCTTTATTATTTTGT |
| ATAATCTTTAAGCAGTCCTCAGGAGGGGACCCAGAAATTGTAACGCACAGTTTT<br>TATTAGAAATTCGTCAGGAGTCCTCCCCTGGGTCTTTAACATTGCGTGTCAAAA |
| AATTGTGGAGGGGAATTTTTCTACTGTAATTCAACACAACTGTTTAATAGTACT<br>TTAACACCTCCCCTTAAAAAGATGACATTAAGTTGTGTTGACAAATTATCATGA |
| TGGTTTAATAGTACTTGGAGTACTAAAGGGTCAAATAACACTGAAGGAAGTGAC<br>ACCAAATTATCATGAACCTCATGATTTCCCAGTTTATTGTGACTTCCTTCACTG |
| ACAATCACCCTCCCATGCAGAATAAAACAAATTATAAACATGTGGCAGGAAGTA<br>TGTTAGTGGGAGGGTACGTCTTATTTTGTTTAATATTTGTACACCGTCCTTCAT |
| GGAAAAGCAATGTATGCCCCTCCCATCAGTGGACAAATTAGATGTTCATCAAAT<br>CCTTTTCGTTACATACGGGGAGGGTAGTCACCTGTTTAATCTACAAGTAGTTTA |
| ATTACAGGGCTGCTATTAACAAGAGATGGTGGTAATAGCAACAATGAGTCCGAG<br>TAATGTCCCGACGATAATTGTTCTCTACCACCATTATCGTTGTTACTCAGGCTC |
| ATCTTCAGACCTGGAGGAGGAGATATGAGGGACAATTGGAGAAGTGAATTATAT<br>TAGAAGTCTGGACCTCCTCCTCTATACTCCCTGTTAACCTCTTCACTTAATATA |
| AAATATAAAGTAGTAAAAATTGAACCATTAGGAGTAGCACCCACCAAGGCAAAG<br>TTTATATTTCATCATTTTTAACTTGGTAATCCTCATCGTGGGTGGTTCCGTTTC |
| AGAAGAGTGGTGCAGAGAGAAAAAAGAGCAGTGGGAATAGGAGCTTTGTTCCTT<br>TCTTCTCACCACGTCTCTCTTTTTTCTCGTCACCCTTATCCTCGAAACAAGGAA |
| GGGTTCTTGGGAGCAGCAGGAAGCACTATGGGCGCAGCGTCAATGACGCTGACG<br>CCCAAGAACCCTCGTCGTCCTTCGTGATACCCGCGTCGCAGTTACTGCGACTGC |
| GTACAGGCCAGACAATTATTGTCTGGTATAGTGCAGCAGCAGAACAATTTGCTG<br>CATGTCCGGTCTGTTAATAACAGACCATATCACGTCGTCGTCTTGTTAAACGAC |
| AGGGCTATTGAGGCGCAACAGCATCTGTTGCAACTCACAGTCTGGGGCATCAAG<br>TCCCGATAACTCCGCGTTGTCGTAGACAACGTTGAGTGTCAGACCCCGTAGTTC |
| CAGCTCCAGGCAAGAATCCTGGCTGTGGAAAGATACCTAAAGGATCAACAGCTC<br>GTCGAGGTCCGTTCTTAGGACCGACACCTTTCTATGGATTTCCTAGTTGTCGAG |
| CTGGGGATTTGGGGTTGCTCTGGAAAACTCATTTGCACCACTGCTGTGCCTTGG<br>GACCCCTAAACCCCAACGAGACCTTTTGAGTAAACGTGGTGACGACACGGAACC |
| AATGCTAGTTGGAGTAATAAATCTCTGGAACAGATTTGGAATAACATGACCTGG<br>TTACGATCAACCTCATTATTTAGAGACCTTGTCTAAACCTTATTGTACTGGACC |
| ATGGAGTGGGACAGAGAAATTAACAATTACACAAGCTTCCCGGGAGCTCGAATT<br>TACCTCACCCTGTCTCTTTAATTGTTAATGTGTTCGAAGGGCCCTCGAGCTTAA |
| CTTGAAGACGAAAGGGCCTCG<br>GAACTTCTGCTTTCCCGGAGC |

TABLE 12

| Amino acid sequence of HIV portion of protein KH1 |
|---|
| MetValTrpLysGluAlaThrThrThrLeuPheCysAlaSerAspAlaLysAlaTyr<br>AspThrGluValHisAsnValTrpAlaThrHisAlaCysValProThrAspPro<br>AsnProGlnGluValValLeuValAsnValThrGluAsnPheAsnMetTrpLys<br>AsnAspMetValGluGlnMetHisGluAspIleIleSerLeuTrpAspGlnSer<br>LeuLysProCysValLysLeuThrProLeuCysValSerLeuLysCysThrAsp<br>LeuLysAsnAspThrAsnThrAsnSerSerSerGlyArgMetIleMetGluLys<br>GlyGluIleLysAsnCysSerPheAsnIleSerThrSerIleArgGlyLysVal<br>GlnLysGluTyrAlaPhePheTyrLysLeuAspIleIleProIleAspAsnAsp<br>ThrThrSerTyrThrLeuThrSerCysAsnThrSerValIleThrGlnAlaCys<br>ProLysValSerPheGluProIleProIleHisTyrCysAlaProAlaGlyPhe<br>AlaIleLeuLysCysAsnAsnLysThrPheAsnGlyThrGlyProCysThrAsn<br>ValSerThrValGlnCysThrHisGlyIleArgProValValSerThrGlnLeu<br>LeuLeuAsnGlySerLeuAlaGluGluGluValValIleArgSerAlaAsnPhe<br>ThrAspAsnAlaLysThrIleIleValGlnLeuAsnGlnSerValGluIleAsn<br>CysThrArgProAsnAsnAsnThrArgLysSerIleArgIleGlnArgGlyPro<br>GlyArgAlaPheValThrIleGlyLysIleGlyAsnMetArgGlnAlaHisCys<br>AsnIleSerArgAlaLysTrpAsnAsnThrLeuLysGlnIleAspSerLysLeu<br>ArgGluGlnPheGlyAsnAsnLysThrIleIlePheLysGlnSerSerGlyGly<br>AspProGluIleValThrHisSerPheAsnCysGlyGlyGluPhePheTyrCys<br>AsnSerThrGlnLeuPheAsnSerThrTrpPheAsnSerThrTrpSerThrLys<br>GlySerAsnAsnThrGluGlySerAspThrIleThrLeuProCysArgIleLys<br>GlnIleIleAsnMetTrpGlnGluValGlyLysAlaMetTyrAlaProProIle |

TABLE 12-continued

| Amino acid sequence of HIV portion of protein KH1 |
|---|
| SerGlyGlnIleArgCysSerSerAsnIleThrGlyLeuLeuLeuThrArgAsp<br>GlyGlyAsnSerAsnAsnGluSerGluIlePheArgProGlyGlyGlyAspMet<br>ArgAspAsnTrpArgSerGluLeuTyrLysTyrLysValValLysIleGluPro<br>LeuGlyValAlaProThrLysAlaLysArgArgValValGlnArgGluLysArg<br>AlaValGlyIleGlyAlaLeuPheLeuGlyPheLeuGlyAlaAlaGlySerThr<br>MetGlyAlaAlaSerMetThrLeuThrValGlnAlaArgGlnLeuLeuSerGly<br>IleValGlnGlnGlnAsnAsnLeuLeuArgAlaIleGluAlaGlnGlnHisLeu<br>LeuGlnLeuThrValTrpGlyIleLysGlnLeuGlnAlaArgIleLeuAlaVal<br>GluArgTyrLeuLysAspGlnGlnLeuLeuGlyIleTrpGlyCysSerGlyLys<br>LeuIleCysThrThrAlaValProTrpAsnAlaSerTrpSerAsnLysSerLeu<br>GluGlnIleTrpAsnAsnMetThrTrpMetGluTrpAspArgGluIleAsnAsn<br>TryThr |

TABLE 12a

| Nucleotide sequence encoding HIV portion of protein KH1 |
|---|
| ATGGTGTGGAAGGAAGCAACCACCACTCTATTTTGTGCATCAGATGCTAAAGCATAT<br>GATACAGAGGTACATAATGTTTGGGCCACACATGCCTGTGTACCCACAGACCCC<br>AACCCACAAGAAGTAGTATTGGTAAATGTGACAGAAAATTTTAACATGTGGAAA<br>AATGACATGGTAGAACAGATGCATGAGGATATAATCAGTTTATGGGATCAAAGC<br>CTAAAGCCATGTGTAAAATTAACCCCACTCTGTGTTAGTTTAAAGTGCACTGAT<br>TTGAAGAATGATACTAATACCAATAGTAGTAGCGGGAGAATGATAATGGAGAAA<br>GGAGAGATAAAAAACTGCTCTTTCAATATCAGCACAAGCATAAGAGGTAAGGTG<br>CAGAAAGAATATGCATTTTTTTATAAACTTGATATAATACCAATAGATAATGAT<br>ACTACCAGCTATACGTTGACAAGTTGTAACACCTCAGTCATTACACAGGCCTGT<br>CCAAAGGTATCCTTTGAGCCAATTCCCATACATTATTGTGCCCCGGCTGGTTTT<br>GCGATTCTAAAATGTAATAATAAGACGTTCAATGGAACAGGACCATGTACAAAT<br>GTCAGCACAGTACAATGTACACATGGAATTAGGCCAGTAGTATCAACTCAACTG<br>CTGTTAAATGGCAGTCTGGCAGAAGAAGAGGTAGTAATTAGATCTGCCAATTTC<br>ACAGACAATGCTAAAACCATAATAGTACAGCTGAACCAATCTGTAGAAATTAAT<br>TGTACAAGACCCAACAACAATACAAGAAAAAGTATCCGTATCCAGAGAGGACCA<br>GGGAGAGCATTTGTTACAATAGGAAAAATAGGAAATATGAGACAAGCACATTGT<br>AACATTAGTAGAGCAAAATGGAATAACACTTTAAAACAGATAGATAGCAAATTA<br>AGAGAACAATTTGGAAATAATAAAACAATAATCTTTAAGCAGTCCTCAGGAGGG<br>GACCCAGAAATTGTAACGCACAGTTTTAATTGTGGAGGGGAATTTTTCTACTGT<br>AATTCAACACAACTGTTTAATAGTACTTGGTTTAATAGTACTTGGAGTACTAAA<br>GGGTCAAATAACACTGAAGGAAGTGACACAATCACCCTCCCATGCAGAATAAAA<br>CAAATTATAAACATGTGGCAGGAAGTAGGAAAAGCAATGTATGCCCCTCCCATC<br>AGTGGACAAATTAGATGTTCATCAAATATTACAGGGCTGCTATTAACAAGAGAT<br>GGTGGTAATAGCAACAATGAGTCCGAGATCTTCAGACCTGGAGGAGGAGATATG<br>AGGGACAATTGGAGAAGTGAATTATATAAATATAAAGTAGTAAAAATTGAACCA<br>TTAGGAGTAGCACCCACCAAGGCAAAGAGAAGAGTGGTGCAGAGAGAAAAAAGA<br>GCAGTGGGAATAGGAGCTTTGTTCCTTGGGTTCTTGGGAGCAGCAGGAAGCACT<br>ATGGGCGCAGCGTCAATGACGCTGACGGTACAGGCCAGACAATTATTGTCTGGT<br>ATAGTGCAGCAGCAGAACAATTTGCTGAGGGCTATTGAGGCGCAACAGCATCTG<br>TTGCAACTCACAGTCTGGGGCATCAAGCAGCTCCAGGCAAGAATCCTGGCTGTG<br>GAAAGATACCTAAAGGATCAACAGCTCCTGGGGATTTGGGGTTGCTCTGGAAAA<br>CTCATTTGCACCACTGCTGTGCCTTGGAATGCTAGTTGGAGTAATAAATCTCTG<br>GAACAGATTTGGAATAACATGACCTGGATGGAGTGGGACAGAGAAATTAACAAT<br>TACACA |

We claim:

1. An immunological assay for detecting or quantifying antibody against HTLV-III in a fluid comprising using a protein selected from the group consisting of the HTLV-III protein portion of R10, consisting of the sequence listed in FIG. 6; the HTLV-III protein portion of PB1, consisting of the sequence listed in FIG. 8; and the HTLV-III protein portion of 590, consisting of the sequence listed in FIG. 10 to contact a fluid sample; and determining if antibody is bound to said protein as an indication of anti-HTLV-III in the sample.

2. An immunochemical assay, according to claim 1, wherein said HTLV-III protein portion is from R10.

3. An immunochemical assay, according to claim 1, wherein said protein is the HTLV-III protein portion from PB1, consisting of the sequence listed in FIG. 8.

4. An immunochemical assay, according to claim 1, wherein said HTLV-III protein portion is from 590.

5. A method of detecting antibody against HTLV-III in a biological fluid, comprising the steps of:

(a) incubating an immunoadsorbent comprising a solid phase to which is attached a protein selected from the group consisting of the HTLV-III protein portion of R10, consisting of the sequence listed in FIG. 6; the HTLV-III protein portion of PB1, consisting of the sequence listed in FIG. 8; and the HTLV-III protein portion of 590, consisting of sequence listed in FIG. 10, with a sample of the biological fluid to be tested, under conditions which allow the anti-HTLV-III antibody in the sample to bind to the immunoadsorbent, thereby using said protein to bind antibody from the sample, if present;

(b) separating the immunoadsorbent from the sample; and (c) determining if antibody has bound to the immunoadsorbent as an indication of anti-HTLV-III in the sample.

6. A method of claim 5, wherein the step of determining if antibody has bound to the immunoadsorbent comprises incubating the immunoadsorbent with a labeled antibody against antigen of the species from which the biological fluid is derived; thereafter separating the immunoadsorbent from the labeled antibody after the incubation period; and detecting the label associated with the immunoadsorbent.

7. A method of claim 5, wherein the step of determining if antibody has bound to the immunoadsorbent comprises incubating the immunoadsorbent with a labeled protein selected from the group consisting of the HTLV-III protein portion of R10, consisting of sequence in Table 12; the HTLV-III protein portion of PB1, consisting of the sequence listed in FIG. 8; and the HTLV-III protein portion of 590, consisting of the sequence listed in FIG. 10; separating the immunoadsorbent from the labeled protein; and detecting the label associated with the immunoadsorbent.

8. A method of claim 5, wherein the step of determining if antibody has bound to the immunoadsorbent comprises incubating the immunoadsorbent with labeled protein A; separating the immunoadsorbent from the labeled protein A; and detecting the label associated with the immunoadsorbent.

9. A method of detecting antibody against HTLV-III in a human serum or plasma sample, comprising the steps of:
(a) providing an immunoadsorbent comprising a bead coated with a protein selected from the group consisting of the HTLV-III protein portion of R10, consisting of the sequence listed in FIG. 6; the HTLV-III protein portion of PB1, consisting of the sequence listed in FIG. 8; and the HTLV-III protein portion of 590, consisting of the sequence listed in FIG. 10;
(b) incubating the immunoadsorbent, with the serum or plasma sample under conditions which allow anti-HTLV-III antibody in the sample to bind the immunoadsorbent, thereby using said protein to bind antibody in the sample if present;
(c) separating the immunoadsorbent and the sample;
(d) incubating the immunoadsorbent with a labeled anti-(human IgG) antibody under conditions which allow the anti-(human IgG) antibody to bind human anti-HTLV-III antibody bound to the immunoadsorbent,
(e) separating the immunoadsorbent from the unbound anti-(human IgG) antibody; and
(f) evaluating the label associated with the immunoadsorbent as an indication of the presence of antibody against HTLV-III in the sample.

10. A method of claim 9, wherein the immunoadsorbent further comprises a blocking protein.

11. A method of claim 9, wherein the labeled anti-(human IgG) antibody is an animal antibody and the serum or plasma sample is diluted with normal serum of an animal of the same species.

12. A method of claim 9, wherein the anti-(human IgG) antibody is a goat antibody and the serum or plasma sample is diluted with normal goat serum.

13. A method of claim 9, wherein the anti-(human IgG) antibody is labeled with a radioisotope, an enzyme or a fluorescent compound.

14. An immunoadsorbent for use in a solid phase immunochemical assay for antibody against HTLV-III, comprising a solid phase to which is affixed a protein selected from the group consisting of the HTLV-III protein portion of R10, consisting of the sequence listed in FIG. 6; the HTLV-III protein portion of PB1, consisting of the sequence listed in FIG. 9, and the HTLV-III protein portion of 590, consisting of the sequence listed in FIG. 10.

15. An immunoadsorbent of claim 14, wherein the solid phase is a glass or plastic bead, a well of a microtiter plate or a test tube.

16. An immunoadsorbent of claim 14, further comprising a blocking protein.

17. A kit for use in detecting antibody against HTLV-III in a biological fluid comprising:
(a) an immunoadsorbent comprising a solid phase to which is attached at least one protein selected from the group consisting of the HTLV-III protein portion of R10, consisting of sequence listed in FIG. 6; the HTLV-III protein portion of PB1, consisting of the sequence listed in FIG. 8; and the HTLV-III protein portion of 590, consisting of the sequence listed in FIG. 10, which can be used to contact a sample of the biological fluid to be tested, under conditions which allow the anti-HTLV-III antibody in the sample to bind to the immunoadsorbent; and
(b) labeled HTLV-III antibody.

18. The kit of claim 17, wherein the anti-HTLV-III antibody is labeled with anti(human IgG) antibody as a detectable label.

* * * * *

UNITED STATES PATENT AND TRADEMARK OFFICE
CERTIFICATE OF CORRECTION

PATENT NO. : 5,262,301
DATED : November 16, 1993
INVENTOR(S) : Putney et al

It is certified that error appears in the above-indentified patent and that said Letters Patent is hereby corrected as shown below:

Column 1, line 47: Delete "Beudoin" and insert --Beaudoin--.
Column 2, line 46: Delete "site tot he BGlIII site" and insert --site to the BglIII site--
Column 2, line 57: Delete "HindII" and insert --HindIII--
Column 3, line 37: Delete "constituted a license" and insert --constitute a license-
Column 4, line 14: Delete "FMOS" and insert --FMOC--
Column 6, line 24: Delete "to be test" and insert --to be tested--
Column 6, line 27: Delete "The diluene plasma" and insert --The diluent plasma--
Column 9, line 63-64: Delete "This declaration inactivities the rop" and insert --This deletion inactivate the rop--
Column 11, line 38: Delete "the 4' end" and insert --the 5' end--
Column 11, line 39: Delete "overhand" and insert --overhang--
Column 11, line 53: Delete "patter" and insert --pattern--
Column 12, line 42: Delete "(pharmacia" and insert --(Pharmacia--
Column 12, line 47: Delete "0-0.8% NaCl" and insert --0-0.8M NaCl--
Column 14, line 27: Delete "overhand" and insert --overhang--
Column 14, line 41: Delete "REV2.2" and insert --pREV2.2--
Column 15, line 40: Delete "20 mM potassium phosphate" and insert --20 mM Tris-CL--
Column 15, line 60: Delete "The concentrated" and insert --The concentrate--
Column 16, line 14: Delete "overhand" and insert --overhang--
Column 16, line 16: Delete "polymeraise" and insert --polymerase--
Column 19, line 18: Delete "Stracuch," and insert --Strauch,--
Column 20, line 51: Delete "of al of the" and insert --of all of the--
Column 20, line 53: Delete "a JA-10-rotor" and insert --a JA-10 rotor--
Column 20, line 66: Delete "assuming of 1.0 at 280 nm." and insert --assuming that a 1 mg/ml solution of protein has an absorbance of 1.0 at 280 nm.--

UNITED STATES PATENT AND TRADEMARK OFFICE
CERTIFICATE OF CORRECTION

PATENT NO. : 5,262,301  
DATED : November 16, 1993  
INVENTOR(S) : Putney et al

Page 2 of 2

It is certified that error appears in the above-indentified patent and that said Letters Patent is hereby corrected as shown below:

Columns 31-32, Table 8A, line 40: Delete "CTAGTTGTCCACCAACG TTGACCTGTTCCGTG<u>GTA</u>TCGCCCTGAAACGTTCACCA" and insert --CTAGTTGTCCACCAACGTTGACCTGTTCCGT<u>GAT</u>CGCCCTGAAACGTTCACCA<u>C</u>--

Columns 41-42, Table 11A, line 23: Delete "AACACCTCAGTCATTACACAGG C<u>TT</u>GTCCAAAGGTATCCTTTGAGCCAATTCCC" and insert- AACAAATCAGTCATTACACAGG<u>CC</u>TGTCCAA AGGTATCCTTTGAGCCAATTCCC--

Column 45, line 47: Delete "An immunological" and insert --An immunochemical--  
Column 47, line 9: Delete "in Table 12;" and insert --in Figure 6;--  
Column 48, line 22: Delete "in FIG. 9," and insert --in Fig. 8;--  
Abstract [57], line 2: Delete "R10, RB1, 590" and insert --R10, PB1, 590--  
Abstract [57], line 6: After "fusion protein" insert --; and protein KH1 is a 70 kD fusion protein.--

Signed and Sealed this

Fourth Day of October, 1994

BRUCE LEHMAN

Attest:

Attesting Officer

Commissioner of Patents and Trademarks